United States Patent
Sholder

(10) Patent No.: US 8,112,149 B2
(45) Date of Patent: Feb. 7, 2012

(54) SYSTEM AND METHOD FOR HEART AND ACTIVITY MONITORING

(75) Inventor: Jason Sholder, Fort Lee, NJ (US)

(73) Assignee: Monitoring Information Technologies, Inc., Fort Lee, NJ (US)

(*) Notice: Subject to any disclaimer, the term of this patent is extended or adjusted under 35 U.S.C. 154(b) by 475 days.

(21) Appl. No.: 11/712,284

(22) Filed: Feb. 27, 2007

(65) Prior Publication Data

US 2010/0210953 A1 Aug. 19, 2010

Related U.S. Application Data

(60) Provisional application No. 60/776,834, filed on Feb. 27, 2006.

(51) Int. Cl.
*A61B 5/0456* (2006.01)
(52) U.S. Cl. ........ 600/516; 600/515; 600/517; 600/518; 607/17; 607/18
(58) Field of Classification Search .......... 600/515–518; 607/17–18
See application file for complete search history.

(56) References Cited

U.S. PATENT DOCUMENTS

| | | |
|---|---|---|
| 3,829,782 A | 8/1974 | Dillman |
| 3,937,226 A | 2/1976 | Funke |
| 4,088,140 A | 5/1978 | Rockland |
| 4,374,382 A | 2/1983 | Markowitz |
| 4,503,858 A | 3/1985 | Markowitz |
| 4,505,276 A | 3/1985 | Markowitz |
| 4,556,063 A | 12/1985 | Thompson |
| 4,583,553 A | 4/1986 | Shah et al. |
| 4,618,861 A | 10/1986 | Gettens et al. |
| 4,712,555 A * | 12/1987 | Thornander et al. ........... 607/17 |
| 4,848,352 A | 7/1989 | Pohndorf |
| 4,905,707 A | 3/1990 | Davies |
| 4,911,170 A | 3/1990 | Thomas, III et al. |
| 4,940,052 A | 7/1990 | Mann et al. |
| 4,944,299 A | 7/1990 | Silvian |
| 5,040,534 A | 8/1991 | Mann et al. |
| 5,052,388 A | 10/1991 | Sivula |
| 5,058,597 A | 10/1991 | Onoda et al. |
| 5,074,302 A | 12/1991 | Poore et al. |
| 5,127,404 A | 7/1992 | Wyborny |
| 5,135,004 A | 8/1992 | Adams |
| 5,139,028 A | 8/1992 | Steinhaus |

(Continued)

OTHER PUBLICATIONS

Roland Hetzer, MD, et al.; "Daily Noninvasive Rejection Monitoring Improves Long-Term Survival in Pediatric Heart Transplant";(Oct. 1998); Issue of "Annals of Thoracic Surgery"); (1-8 pgs.).

(Continued)

*Primary Examiner* — Niketa Patel
*Assistant Examiner* — Rex R Holmes
(74) *Attorney, Agent, or Firm* — Morgan, Lewis & Bockius LLP

(57) ABSTRACT

A system and method determining physiological status of a patient. A determination is made whether the patient is sleeping. The amplitude and change in voltage over time of any intramyocardial electrogram is measured for a right ventricle and a left ventricle of a heart of the patient for a predefined number of heartbeats at a specified time interval in response to determining the patient is asleep. The measurements are averaged for the right ventricle and left ventricle. The averaged measurements are transmitted to a receiver for communication to an intended recipient.

28 Claims, 23 Drawing Sheets

U.S. PATENT DOCUMENTS

| | | |
|---|---|---|
| 5,143,065 A | 9/1992 | Adkins et al. |
| 5,157,604 A | 10/1992 | Axfovd et al. |
| 5,197,480 A | 3/1993 | Gebhardt |
| 5,243,981 A | 9/1993 | Hudrlik |
| 5,285,793 A | 2/1994 | Slovut |
| 5,292,341 A | 3/1994 | Snell et al. |
| 5,402,794 A | 4/1995 | Wahlstrand et al. |
| 5,476,483 A | 12/1995 | Bornzin et al. |
| 5,514,162 A | 5/1996 | Bornzin et al. |
| 5,782,890 A | 7/1998 | Wahlstrand et al. |
| 2003/0153956 A1 * | 8/2003 | Park et al. .................. 607/17 |
| 2004/0044374 A1 * | 3/2004 | Weinberg et al. ........... 607/25 |
| 2005/0027320 A1 * | 2/2005 | Nehls et al. .................. 607/9 |
| 2009/0192397 A1 * | 7/2009 | Fischell et al. ............ 600/516 |

OTHER PUBLICATIONS

J. Muller, et al.; "Non-invasive monitoring of rejection after cardiac Transplantation"; DMW Walter Siegenthaler Prize; (2002); (11 pages).

* cited by examiner

807 — Date    April 4 1999

802 — IRAM Serial Number   2347
804 — Patient Number       P144
806 — Protocol             Readings taken every 5 minutes over two hours @ 10 beats/reaqding.

808 — Electrode lead 1
    Average IMEG Amplitude
        9.88 mV
    Average dV/dt (mV/msec)
        10.21 mV/msec

| | | | Minute 5 | | | | | | | | | | | | Minute 10 | | | | | |
|---|---|---|---|---|---|---|---|---|---|---|---|---|---|---|---|---|---|---|---|---|
| 812 — Number of readings | 1 | 2 | 3 | 4 | 5 | 6 | 7 | 8 | 9 | 10 | 1 | 2 | 3 | 4 | 5 | 6 | 7 | 8 | 9 | 10 |
| 814 — IMEG Amplitude (mV) | 9.9 | 9.9 | 9.9 | 9.7 | 9.9 | 9.9 | 9.9 | 9.9 | 9.8 | 10.0 | 9.9 | 9.9 | 9.9 | 9.7 | 9.5 | 9.9 | 9.9 | 9.9 | 9.8 | 10.0 |
| 816 — Average | | | | | 9.88 | | | | | | | | | | 9.84 | | | | | |
| 818 — IMEG Amplitude (mV) | 9.9 | 9.9 | 9.9 | 9.7 | 9.9 | 9.9 | 9.9 | 9.9 | 9.8 | 10.0 | 9.9 | 9.9 | 9.9 | 9.7 | 9.5 | 9.9 | 9.9 | 9.9 | 9.8 | 10.0 |
| 820 — Time (msce) | 0.97 | 0.97 | 0.97 | 0.95 | 0.97 | 0.97 | 0.97 | 0.97 | 0.96 | 0.98 | 0.97 | 0.97 | 0.97 | 0.95 | 0.93 | 0.97 | 0.97 | 0.97 | 0.96 | 0.98 |
| 822 — dV/dt (mV/msec) | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| 824 — Average dV/dt | | | | | 10.21 | | | | | | | | | | 10.21 | | | | | |

○ ○ ○

810 — Electrode lead 2
    Average IMEG Amplitude
        10.20 mV
    Average dV/dt (mV/msec)
        10.54 mV/msec

| | | | Minute 5 | | | | | | | | | | | | Minute 10 | | | | | |
|---|---|---|---|---|---|---|---|---|---|---|---|---|---|---|---|---|---|---|---|---|
| 812 — Number of readings | 1 | 2 | 3 | 4 | 5 | 6 | 7 | 8 | 9 | 10 | 1 | 2 | 3 | 4 | 5 | 6 | 7 | 8 | 9 | 10 |
| 814 — IMEG Amplitude (mV) | 10.2 | 10.1 | 10.2 | 10.1 | 10.2 | 10.3 | 10.1 | 10.1 | 10.2 | 10.1 | 10.2 | 10.4 | 10.2 | 10.2 | 10.2 | 10.1 | 10.2 | 10.2 | 10.6 | 10.2 |
| 816 — Average | | | | | 10.17 | | | | | | | | | | 10.25 | | | | | |
| 818 — IMEG Amplitude (mV) | 10.2 | 10.1 | 10.2 | 10.1 | 10.2 | 10.3 | 10.1 | 10.1 | 10.2 | 10.1 | 10.2 | 10.4 | 10.2 | 10.2 | 10.2 | 10.1 | 10.2 | 10.2 | 10.6 | 10.2 |
| 820 — Time (msce) | 0.97 | 0.97 | 0.97 | 0.95 | 0.97 | 0.94 | 0.97 | 0.97 | 0.96 | 0.98 | 0.97 | 106 | 0.97 | 0.95 | 0.93 | 0.97 | 0.97 | 0.97 | 0.96 | 0.98 |
| 822 — dV/dt (mV/msec) | 0.5 | 0.4 | 0.5 | 0.6 | 110 | 110 | 0.4 | 0.5 | 0.6 | 0.3 | 0.5 | 9.8 | 0.5 | 0.7 | 110 | 110 | 0.5 | 0.5 | 110 | 0.4 |
| 824 — Average dV/dt | | | | | 10.54 | | | | | | | | | | 10.54 | | | | | |

○ ○ ○

FIG. 11
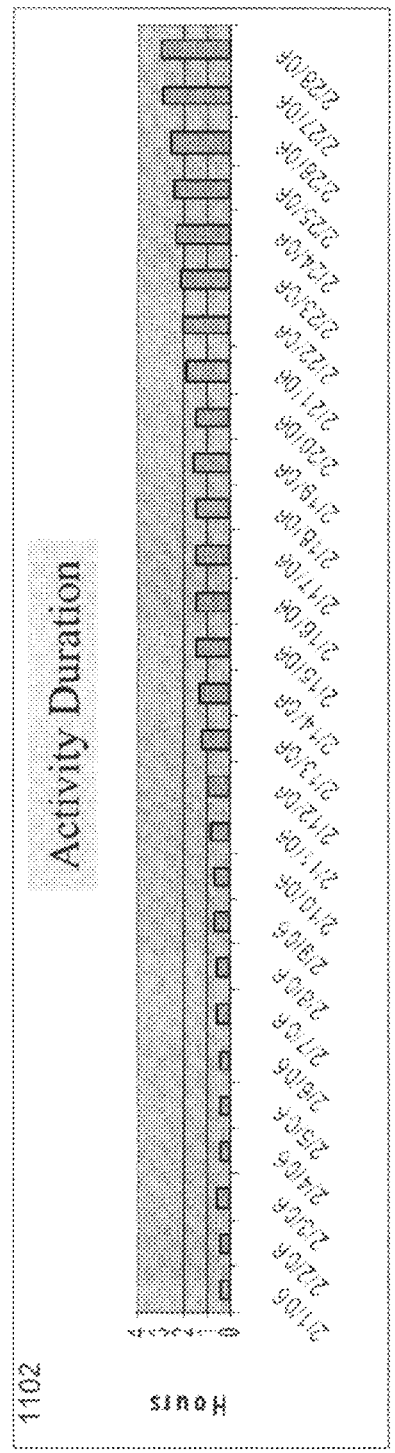
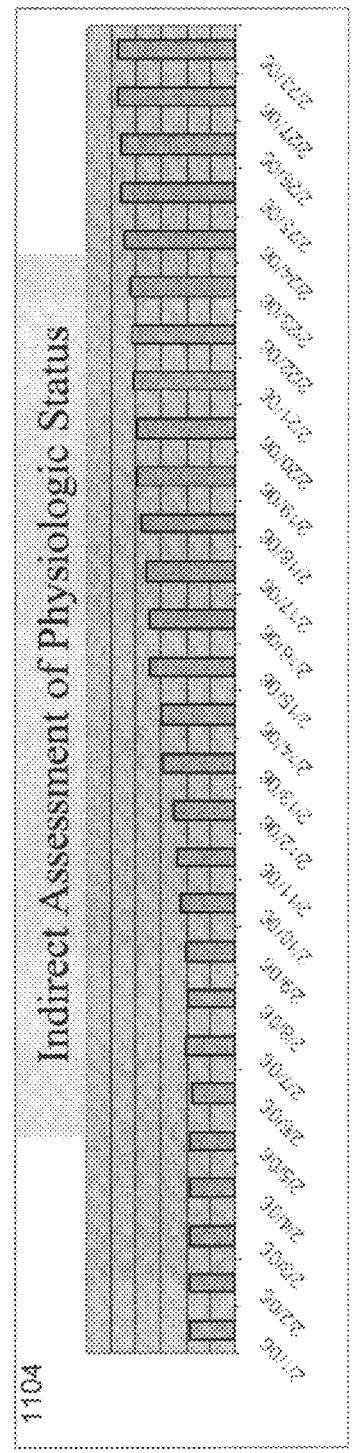
| Combined Sensor | 1-Feb | 2-Feb | 3-Feb | 4-Feb | 5-Feb | 6-Feb | 7-Feb | 8-Feb | 9-Feb | 10-Feb | 11-Feb | 12-Feb |
|---|---|---|---|---|---|---|---|---|---|---|---|---|
| Reciprocal of Sleep | 0.1 | 0.099 | 0.1 | 0.098 | 0.099 | 0.1 | 0.104 | 0.099 | 0.1 | 0.1111 | 0.1235 | 0.125 |
| Exercise level | 3 | 3 | 3 | 3 | 3 | 3 | 3.2 | 3.1 | 3.1 | 3.8 | 3.7 | 3.9 |
| Duration of Exercise | 0.5 | 0.5 | 0.6 | 0.5 | 0.5 | 0.4 | 0.6 | 0.6 | 0.7 | 0.7 | 0.8 | 1 |
| TOTAL | 3.60 | 3.60 | 3.70 | 3.60 | 3.60 | 3.50 | 3.90 | 3.80 | 3.90 | 4.41 | 4.62 | 5.03 |

FIG. 15   Implantation

Patient Information

| Name | Street Address | City | State | Zip |
|---|---|---|---|---|
| Seymour hair | 1414 Balding Dr | Newark | NJ | 07024 |
| Home Tel | Cell Phone | Work Phone | Device Model | Serial Num |
| 201-555-5399 | Same | U81-U812 | QRS 1 | 123456 |

Monitoring Criteria

| Item | < | > | Awake Sleep Both | During Exercise |
|---|---|---|---|---|
| Rate | 50 | 100 | Both | No |
| PR | 80 | 200 | Both | Yes |
| QRS | 100 | 140 | Both | Yes |
| QT | 110 | 490 | Both | Yes |
| PVC/min | N/A | 5 | S | Yes |
| PVC/min | N/A | 10 | A | Yes |
| More PVC | Yes | | Awake | Yes |
| Multiform PVC | No | | Sleep | No |
| | Yes | | Both | Yes |
| Bigeminy | Yes | | Both | Yes |
| Trigeminy | Yes | | Both | Yes |

Tabs: Doctor's Demographics | Patient Listing | New Patient Enrollment | Set Parameters | Billing Friday, February 2, 2010

2200

FIG. 23
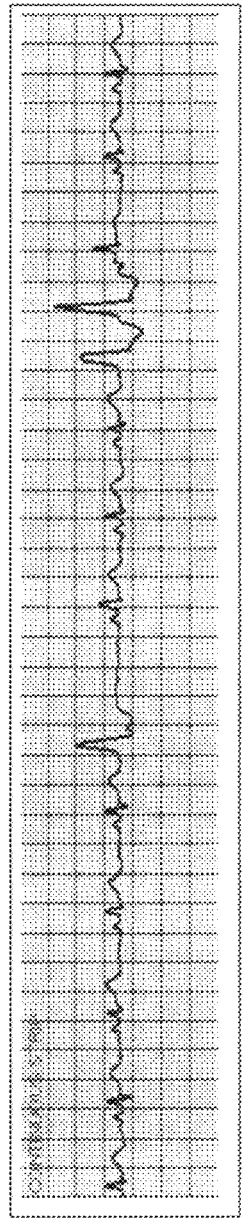
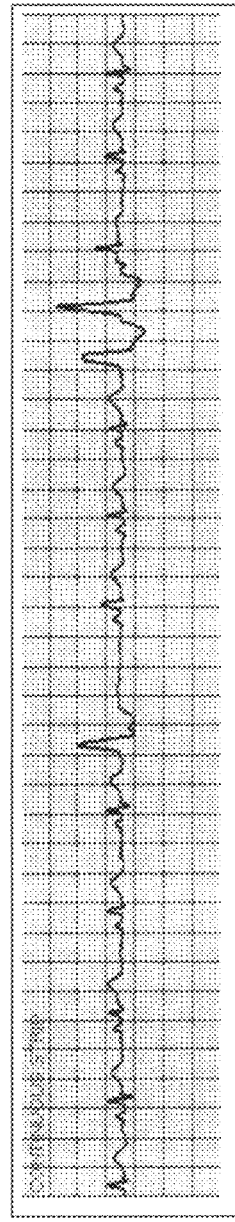

SYSTEM AND METHOD FOR HEART AND ACTIVITY MONITORING

CROSS-REFERENCE TO RELATED APPLICATION

This application claims priority to U.S. Provisional Application No. 60/776,834, filed Feb. 27, 2006, which is hereby incorporated herein by reference.

BACKGROUND OF THE INVENTION

Thousands of people die each year because of heart related problems, including heart disease, heart attack (myocardial infarction), stroke, and heart failure. In many cases, significant heart problems may be corrected through medication, transplant, stenting, valve replacement, medical consultation, or other forms of medical intervention. Medical personnel need an effective method of monitoring the patient's heart for different symptoms, conditions, and parameters in order to provide effective treatment.

For the most part, heart monitoring requires that the patient visit the physician for an electrocardiogram (ECG) and/or other diagnostic tests. Frequently, the ECG by itself is only one of the many diagnostic tools that the physician has in his/her armamentarium, and not adequate alone to diagnose transplant rejection, heart failure, and other heart related disorders.

Current heart monitoring systems provide limited heart monitoring capabilities. Other systems are ineffective at detecting problems because of patient movement, respiration, inspiration, and emotional or physiologic stress. Frequently, traditional methods of heart monitoring are ineffective or incapable of detecting the subtle heart performance metrics that may indicate that heart failure or transplant rejection is present or imminent.

When cardiac events occur infrequently (paroxysmal occurrences), EGG may not be effective in detecting certain heart events, such as arrhythmias, tachycardia (fast than normal heart rate), bradycardia (slower than normal heart rate), premature ventricular contractions (PVC), bigeminy, trigeminy, or other abnormal rhythms.

In many dire situations, a heart transplant is the only option for the patient. For these patients, who are placed on anti-rejection medications, anti-inflammatory medication, and any host of other medications, assessment of transplant rejection is of paramount importance. In order to assess rejection, patients require frequent endomyocardial biopsies (EMB).

An EMB is the process of removing tissue from living patients for microscopic diagnostic examination. An EMB requires that small pieces of heart tissue be removed and examined under a microscope. To get the sample of heart tissue, a doctor places a small catheter or tube into a large vein in the neck or a large artery in the groin, which is then passed into the heart. Tiny pieces of the heart tissue are removed and sent to the lab where they are microscopically examined. Biopsies may also be performed if the doctor suspects a heart related disease not related to transplant, or if the heart is not pumping well for unknown reasons.

Biopsies are invasive, painful and frequently leave large scars. In most cases, heart patients dread the thought of a biopsy which adds to post-operative stress and surgical dissatisfaction. The EMB routine for transplant patients varies from 13 to 22 EMBs in the first year following transplant. This form of transplant monitoring for rejection is the standard of care today, and may be difficult, time consuming, expensive, and painful. A small percentage of yearly EMBs result in patient death. As a result, heart monitoring is still plagued by many difficulties and complications despite the many improved techniques and technologies available in modern medicine.

SUMMARY OF THE INVENTION

To provide additional health monitoring of a patient, a system and method of determining physiological status of a patient is disclosed. A determination is made whether the patient is sleeping. The amplitude and change in voltage over time of any intramyocardial electrogram is measured for a right ventricle and a left ventricle of a heart of the patient for a predefined number of heartbeats at a specified time interval in response to determining the patient is asleep. The measurements are averaged for the right ventricle and left ventricle. The averaged measurements are transmitted to a receiver for communication to an intended recipient.

Another embodiment includes a method for determining activity levels of a patient. An activity level is determined based on activity of the patient. The activity is measured by piezoelectric accelerometers in a surgically implanted monitor. Data is measured and stored regarding time awake and moving, activity amplitude, activity duration, and temperature. The data is transmitted to a receiver.

Yet another embodiment includes a heart monitor. The monitor includes one or more electrodes for sensing electrical cardiac signals from a heart at different locations in the heart. The electrodes include piezoelectric accelerometers for measuring motion of the different locations. One or more amplifiers operatively interconnected to the electrodes are configured to filter the electrical signals received from the electrodes. A monitor piezoelectric accelerometer is configured to measure activity levels of a patient. A processor operatively connected to the amplifiers is configured to control the electrical signals sensed by the electrodes. A storage device is operatively connected to the processor and is configured to store data associated with the electrical signals and activity levels. Telemetry circuitry operatively connected to the processor is configured to wirelessly send the data to a receiver.

BRIEF DESCRIPTION OF THE DRAWINGS

Illustrative embodiments of the present invention are described in detail below with reference to the attached drawing figures, which are incorporated by reference herein and wherein:

FIG. 8 is a sample of heart data in accordance with the illustrative embodiments of the present invention;

FIG. 11 is an example of data recorded by a monitor in accordance with the illustrative embodiments of the present invention;

FIG. 19 is an example page for demographics in a graphical user interface in accordance with the illustrative embodiments of the present invention;

FIG. 22 is an example page for setting parameters in a graphical user interface in accordance with illustrative embodiments of the present invention; and FIG. 23 is an example page for a recorded event in a graphical user interface in accordance with illustrative embodiments of the present invention.

DETAILED DESCRIPTION OF THE DRAWINGS

Figure 1:
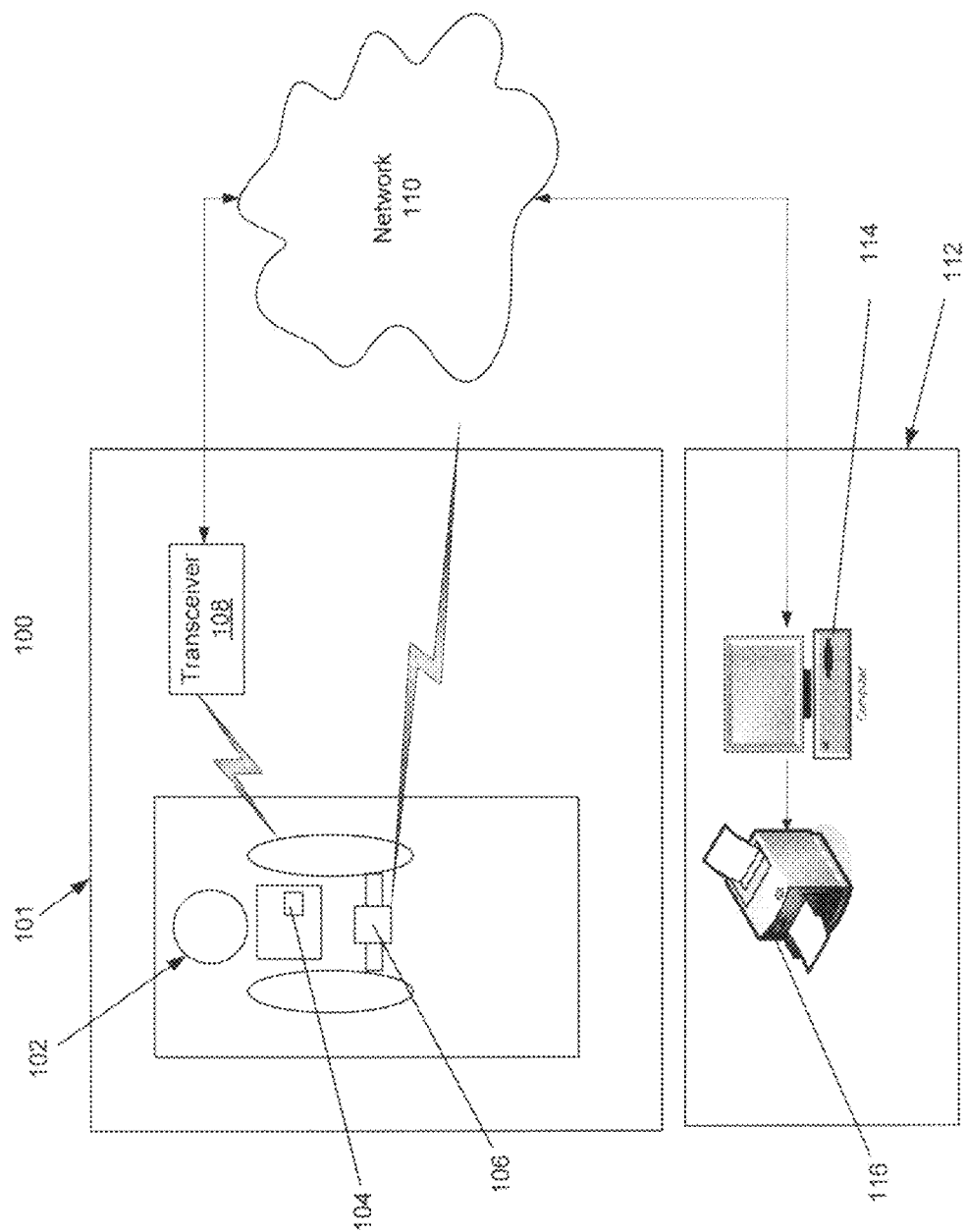
FIG. 1 is a perspective diagram of a health monitoring system in accordance with the illustrative embodiments of the present invention.

FIG. 1 is a perspective diagram of a health monitoring system in accordance with the illustrative embodiments of the present invention. The health monitoring system 100 of FIG. 1 includes various elements including a home 101, a patient 102, a monitor 104, a mobile receiver 106, a transceiver 108, a network 110, a clinic 112, a computer 114, and a printer 116.

The heart monitoring system 100 monitors the health of the patient 102. In particular, the heart monitoring system 100 may be used to monitor the overall physiological status of the patient 102. This includes the status of the patient's heart. For example, the patient 102 may have recently undergone a heart transplant surgery during which the monitor 104 was surgically implanted. As a result, the health monitoring system 100 is able to record heart data including potential symptoms of rejection.

The monitor 104 is surgically implanted in the patient 102 to record, analyze and store vital health information. The monitor 104 may be a physiologic status monitor without leads attached to the patient's heart or may include electrode leads attached to the patient's heart and is further described by FIGS. 4-8. The monitor 104 may function as an Implantable Rejection Assessment Monitor (IRAM) and/or an intramyocardial electrogram (IMEG) monitor. In one embodiment, the monitor 104 may record and store data when the patient 102 is sleeping, resting, or in bed at home 101. This allows the monitor 104 to take more effective measurements because the patient 102 is not experiencing some of the electrocardiographic variations associated with emotional or physiological stress, and other stimulus of wakefulness that may affect effective heart measurements.

Data recorded, analyzed and stored by the monitor 104 may be wirelessly sent to the mobile receiver 106 or the transceiver 108. The health monitor system may include the mobile receiver 106, the transceiver 108, or both based on the needs of the patient 102. The monitor 104 may transmit the data using a low power radio frequency (RF) signal or other data signal for communicating the recorded data to the mobile receiver 106 or the transceiver 108. For example, the data signal may be a Bluetooth® or WiFi® signal or low-power equivalents. The monitor 104, mobile receiver 106, or transceiver 108 may format the data recorded by the monitor 104 for transmission or communication. For example, the transceiver 108 may format the data into packets for transmission across an Internet Protocol (IP) network. In other embodiments, the format may be any communication format suitable for transmitting and reassembling the data sent from the monitor. The monitor may transmit the data to the mobile receiver 106 and transceiver 108 using numerous communication schedules. In one embodiment, the monitor 104 transmits the data at a specified time each morning around the time the patient 102 is waking up from a nights sleep. In another embodiment, the monitor 104 transmits data to the mobile receiver 106 and transceiver 108.

In different embodiments, the monitor 104 may communicate unidirectionally or bidirectionally with the mobile receiver and transceiver 108. For example, the monitor 104 may receive a handshake or verification signal from the mobile receiver 106 or transceiver 108 indicating that data was successfully received during a transmission or that the data needs to be resent because an error, fault, or other problem occurred during transmission. Alternatively, the transceiver 108 may communicate with the monitor 104 to send control signals, update software or logic, or send other parameters for operational or administrative use by the monitor 104.

The mobile receiver 106 may be a battery powered wireless device for receiving data from the monitor 104 and then retransmitting the data to a specified interface. The mobile receiver 106 may be worn by the patient 102 or otherwise attached to the patient 102 or the patient's clothing. The mobile receiver 106 may use general packet radio service (GPRS), a global system for mobile (GSM) communication data transmission technique that transmits data in packets rather than using a continuous channel. GPRS allows the mobile receiver 106 to make efficient use of available radio spectrum.

In one embodiment, the mobile receiver 104 may transmit the data to the transceiver 108. In another embodiment, the mobile receiver 104 may transmit the data through a wireless interface to the network 110. The network 110 may communicate the data to the computer 114 for subsequent analysis by a doctor, technician, or medical specialist. The data may be stored in a database internal to the computer 114 or externally connected. The wireless interface may be a network server, website, or other interface that receives the data before communicating it to the computer 114.

The transceiver 108 is a combination of hardware and software elements that receives data from the monitor 104. In one embodiment, the transceiver communicates unidirectionally. In other embodiments, the transceiver 108 may both send and receive data through the network 110. The transceiver 108 may incorporate communications hardware, such as a local area network card, modem, or other similar telemetry components for sending and receiving data through the network 110. The network 110 may be a private, public, hardwired, wireless, or virtual network or any combination thereof. The transceiver 108 may be connected to the network wirelessly or through a wired connection, such as a dial-up, cable, DSL, or other connection. A wireless connection may be WiFi, WiMAX, satellite, or other wireless or cellular technology. For example, transceiver 108 may be connected to a DSL line that communicates with the computer 114 through the network 110, wherein the network 110 is the Internet.

The computer 114 may be a computing device equipped to receive data from a network. The computer 114 may be a desktop computer, laptop, personal digital assistant (PDA), cellular phone, or other data processing system. The computer 114 may include software or hardware for reconstructing the data for display to a doctor or other user. The computer 114 may include a graphical user interface or web browsing application for accessing the data from the monitor 104. In one embodiment, the data from the monitor 104 may be stored in a web server that is part of the network 110. The computer 114 may use a communications line to access, download, archive, or otherwise use the data. For example, when the patient comes to the clinic 112 to visit with the doctor, the doctor may use the computer 114 to show the patient 102 heart and activity levels. Alternatively, the computer 114 may send data to the interconnected or wireless printer 116 to view a hard copy of the data, data graphs, or other information.

Figure 2A:
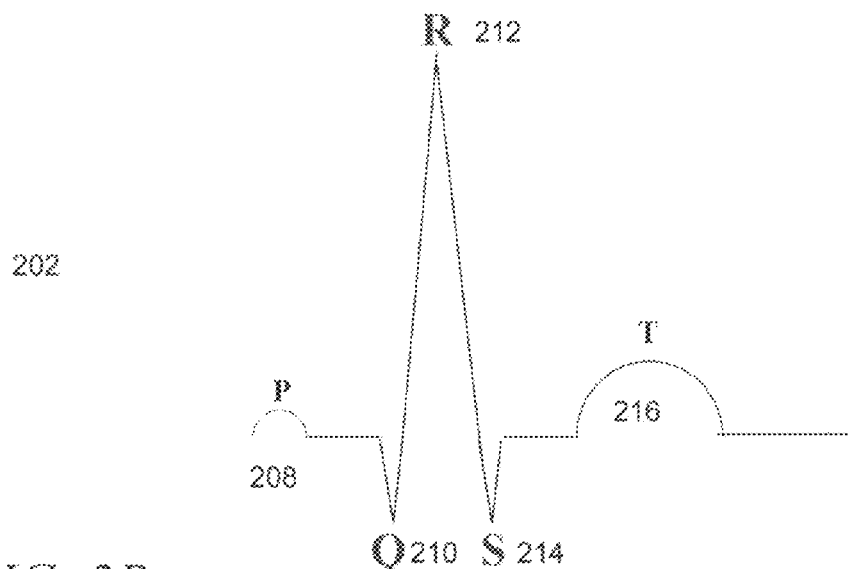
FIGS. 2A-C represent heart wave forms in accordance with the illustrative embodiments of the present invention.
Figure 2B:
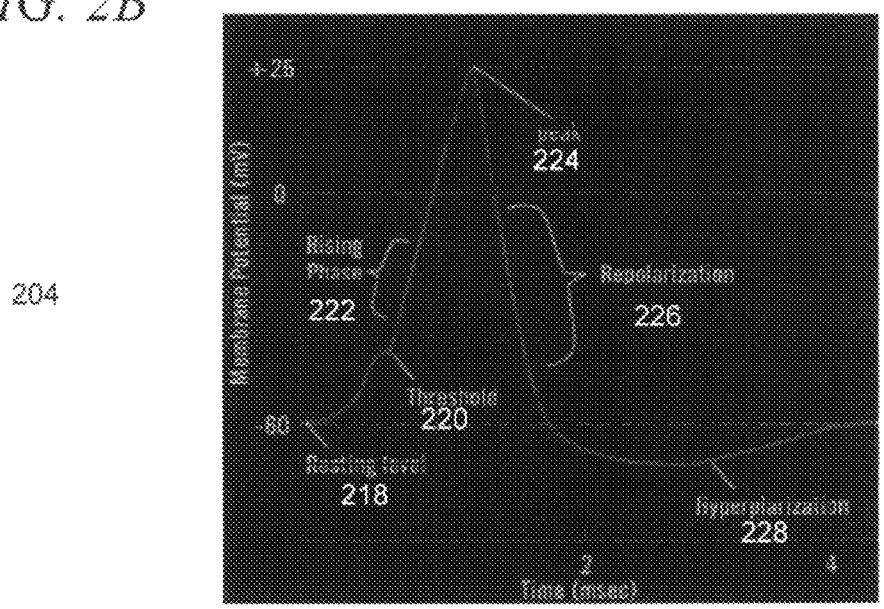
Figure 2C:
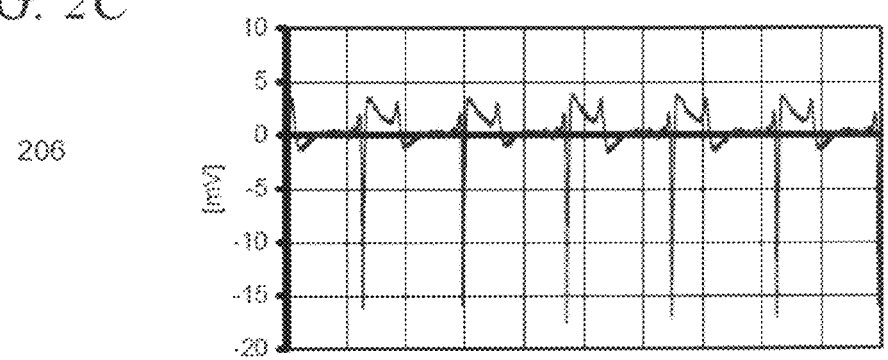

FIGS. 2A-C represent heart wave forms in accordance with the illustrative embodiments of the present invention. FIGS. 2A-C may be measured by a heart monitor, such as monitor 104 of FIG. 1. FIGS. 2A-C include waveforms 202, 204, and 206. The waveforms 202, 204 and 206 may be measured by one or more electrode leads attached to the heart. The electrode lead may be attached to the right and left ventricles of the heart in various positions. For example, the electrode leads may be mechanically attached to the myocardial muscle of the heart or they may be floating inside the ventricle of the heart. The waveforms 202, 204, and 206 represent the depolarization and repolarization of cells in the neuromuscular fibers that result in contractions of the heart. As a result, the waveforms 202, 204, and 206 represent the electrical activity of a cellular contraction and an action potential. This activity occurs because of the interaction of sodium and potassium within a membrane. Neuromuscular fibers both conduct electrical signals and are muscular fibers that contract.

In FIG. 2A the P wave 208 represents atrial electrical activity which causes the atrium of the heart to contract. The depolarization of the ventricle is the electrical signal that causes ventricular contraction as represented by the Q wave 210, R wave 212, and S wave 214. The T wave 216 represents the electrical repolarization of the ventricles.

In FIG. 2B waveform 204 shows the leading edge of a cellular action potential including the resting level 218, threshold 220, rising phase 222, peak 224, repolarization 226, and hyperpolarization 228. The rise time or derivative of the voltage (dV/dt) of this leading edge changes when a transplanted heart experiences the onset of rejection when the amplitude may or may not change. Because these signals are in a higher frequency domain than that measured with a standard electrocardiographic recorder, approximately 0.05 to 150 Hz, it is imperative to have a wider upper frequency spectrum. The monitor amplifier used to view this signal should cover a frequency of 2-3 Hz at the low end to 250 to 300 Hz at the upper end. The resting level 218 is the fully repolarized level before any new contractions may occur. The threshold 220 is when the electrochemical reaction of sodium and potassium reaches a point at which cellular contraction is initiated. The rising phase 222 is particularly important because it is the measure of the change in voltage over time recorded by the monitor. The rising phase 222 may also be referred to as the rise time or slope. The monitor is able to measure the change in voltage during the rise time.

The rise time is the time that passes between the threshold 220 and the peak 224. For example, if dV/dt is changing from 10 mv/1 ms to 10 mv/1.5 ms, indicating a slower cellular signal propagation time, a heart transplant patient may be experiencing signs of rejection. In another example, when a patient's dV/dt decreases, the patient's heart may be showing signs of an upcoming cardiac event.

Hyperpolarization 228 is the voltage level below that of the resting potential. The measurement of hyperpolarization sometimes appears on a surface electrocardiogram as an elevation or depression of the voltage measured between the Q wave 210 and the T wave 216. Changes in this value may indicate cardiac ischemia or poor myocardial oxygenation.

Most heart monitors only measure the peak 224 associated with the amplitude. Heart monitors are unable to measure the slope of the waveform 204 with an ECG machine having a high end frequency of approximately 150 HZ because the frequency component of interest is above 200 Hz. The amplitude may change based on electrode position which may vary as the patient breaths and the heart contracts. However, the slope and rise time is relatively constant even when the amplitude changes.

In FIG. 2C waveform 206 represents multiple, repetitive waveforms similar to the single waveform 204, but as measured by an IRAM with a frequency response of 2-3 Hz at the low end to 250-300 Hz at the upper end.

Figure 3:
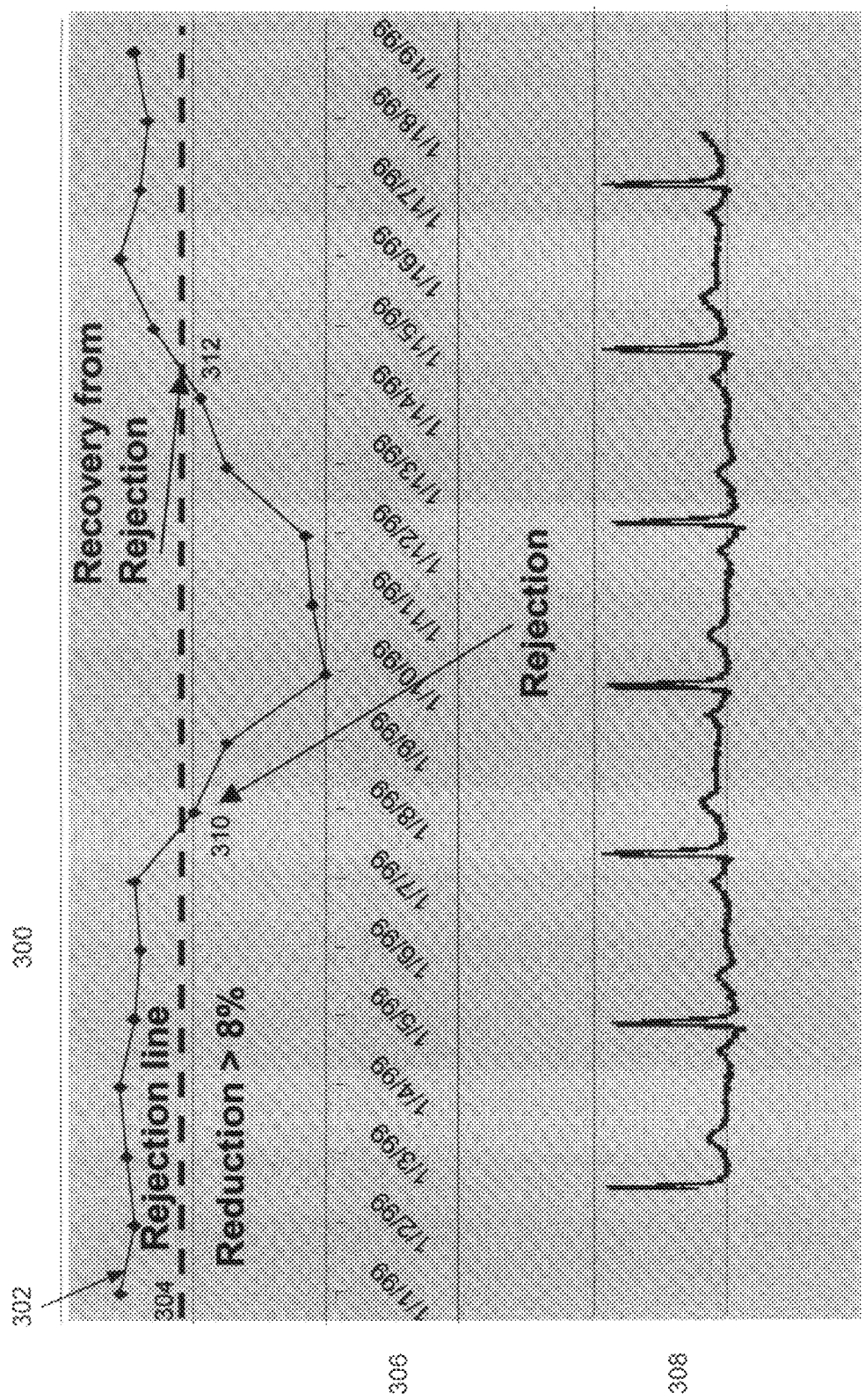
FIG. 3 is a graph illustrating heart rejection in accordance with the illustrative embodiments of the present invention.

FIG. 3 is a graph illustrating heart rejection in accordance with the illustrative embodiments of the present invention. Graph 300 shows various elements including IMEG amplitude and dV/dt 302, rejection line 304, timeline 306, heartbeat waveform 308, and points 310 and 312. Graph 300 illustrates that even though the amplitude of the heartbeat waveform 308 as measured by an intramyocardial electrogram remains relatively consistent as shown by the heartbeat waveform, the patient begins to experience rejection at point 310. Therefore, measuring amplitude alone is not as effective as measuring both amplitude and slope in order to detect rejection.

A monitor, such as monitor 104 of FIG. 1, may be used to measure the change in voltage of the heartbeat waveform 308 over time or dV/dt. As described in FIGS. 2A-B, as the IMEG amplitude and dV/dt 302 begin to decrease, the dV/dt of the heartbeat waveform 308 begins to decrease indicating that rejection or a significant cardiac event is likely to occur. Even though amplitude of the heartbeat waveform 308 may not indicate rejection is likely, by measuring the change in voltage measured over time, a doctor may more effectively prescribe medications and take other actions to prevent rejection, illness, or death of the patient. By detecting symptoms of rejection early the monitor allows the doctor more flexibility in treating the patient and the doctor may not be required to use extreme levels of steroids, antibiotics, and other cardioactive pharmaceuticals that may not be best for the patient's overall well-being.

Figure 4:
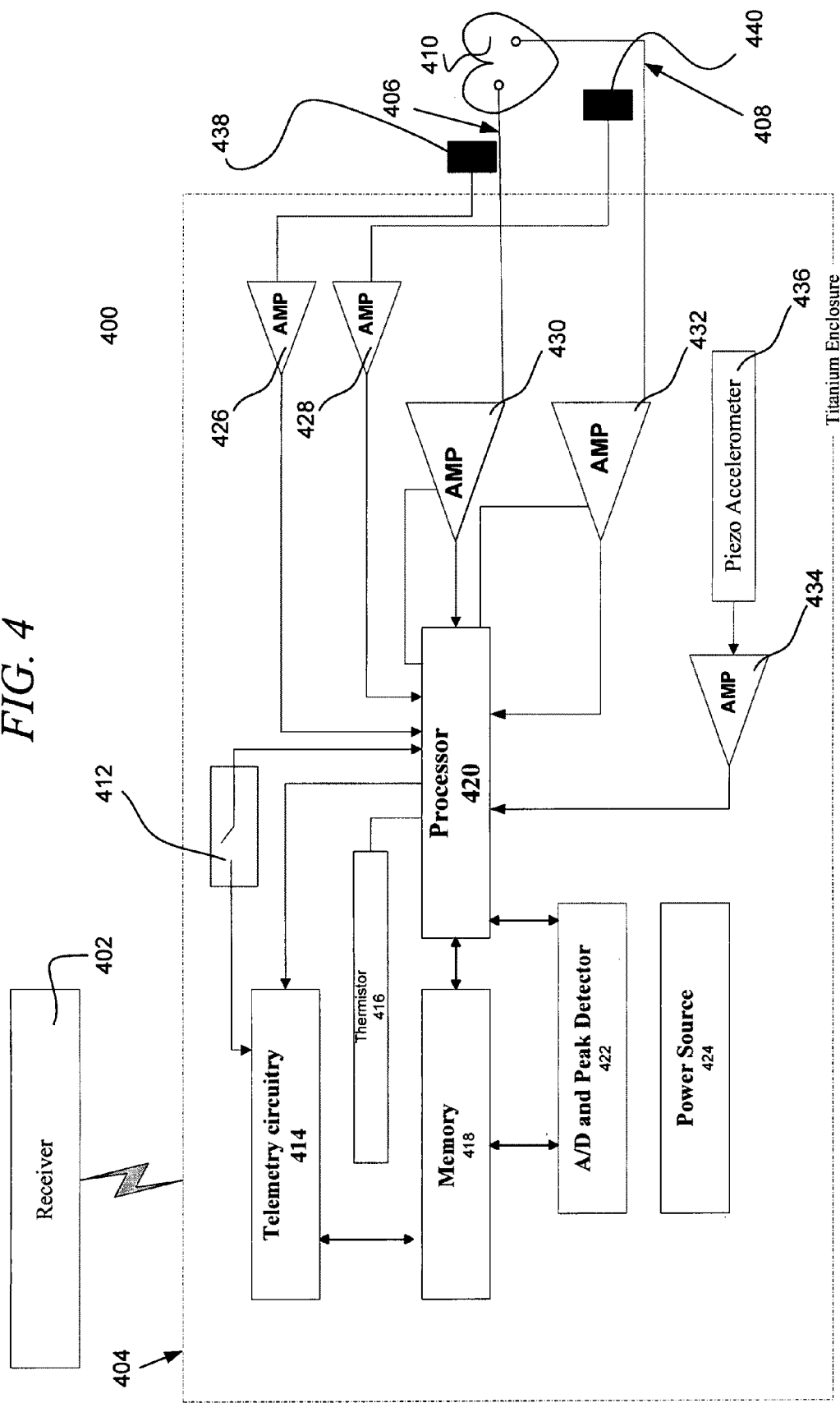
FIG. 4 is a block diagram of a monitor system in accordance with the illustrative embodiments of the present invention.

FIG. 4 is a block diagram of a monitor system in accordance with the illustrative embodiments of the present invention. The monitor system 400 includes various elements including a receiver 402, a heart monitor 404, electrode leads 406 and 408, and a heart 410. The receiver 402 is a particular implementation of the portable receiver 106 or the transceiver 110 of FIG. 1. The heart monitor 404 and electrode leads 406 and 408 are particular implementations of the monitor 104 of FIG. 1. The elements of the heart monitor 404 may be discrete components or may be a single integrated circuit that may be programmed or otherwise configured with various hardware, software and firmware surgically implanted in situ.

The heart monitor 404 further includes a magnetic reed switch 412, telemetry circuitry 414, a thermistor 416, a memory 418, a processor 420, analog to digital converters (A/D) and peak detector 422, amplifiers (amp) 426, 428, 430, 432, and 434, and piezoelectric accelerometer 436. The electrode leads 406 and 408 further include piezoelectric accelerometers 438 and 440. The heart monitor 404 may be an internal heart monitor (IHM), implantable rejection assessment monitor (IRAM), an implantable heart failure monitor (IHFM), an implantable transient event recorder (ITER), or an external transient event recorder (ETER). In one embodiment, the electrode leads 406 and 408 may be connected to the heart 410 using the electrode leads 406 and 408. In other embodiments, external ECG electrodes are employed or the heart monitor 404 may not require electrodes to monitor the patient. Each embodiment may include one or more leads and the number of the amplifiers 426, 428, 430, and 432 may also vary based on whether the piezoelectric accelerometers are integrated as part of the electrode leads 406 and 408.

The receiver 402 may be an external telemetry device for wirelessly receiving data from the heart monitor 404. The receiver 402 may include a memory, logic, processor, and other circuitry and software for receiving and processing data from the heart monitor 404. The receiver 402 may also send data to the heart monitor 404, including a handshake, software, programming, and parameter updates as previously described. In one embodiment, the receiver 402 may include a series of colored lights or a screen for displaying text that may indicate whether data has been sent and received. The colored lights may also specify whether the patient needs to call the doctor based on the received data. For example, if everything is received and transmitted correctly a green light may be displayed. If a red light is displayed, the receiver 402 may indicate that the patient needs to call the doctor as soon as possible.

In one embodiment, the receiver may include memory and logic for determining whether the received data indicates rejection, a heart event, or other condition that warrants immediate action by the patient or the patient's doctor. For example, a text display may tell the patient to "take an extra dose of antibiotics, aspirin, and call your doctor".

The heart monitor 404 may be formed from a titanium enclosure. Titanium produces on its own, titanium oxide, which is body-compatible and is used in conventional cardiac pacemakers. The heart monitor 404 may also be plastic or a composite. All of the components within the heart monitor 404 are body compatible and are secured in place. The implantable heart monitor 404 is vacuum sealed and impervious to body fluids. The electrode leads 406 and 408 connect to the heart monitor 404 through a glass-to-metal feed-through, or some other acceptable feed-through that allows the electrode leads 406 and 408 to be connected to the internal electronics of the heart monitor 404.

The power source 424 may be a battery or other power device. In one embodiment, the power source 424 is a lithium iodine or lithium silver chromate battery because of the extremely long battery life. Alternatively, the power source 424 may be any other solid state power device based on the power requirements.

The processor 420 is a micro processing device or unit for performing calculations, analysis, and coordinating the operation and control of the heart monitor 404. The processor 420 may include logic for controlling the functions and monitoring capabilities of the IRAM 420. The thermistor 416 may be a thermometer or a variety of temperature sensitive semiconductor elements. The thermistor 416 allows the heart monitor 404 to determine the patient's temperature which may indicate whether there is any infection or whether symptoms are temperature related.

The memory 418 is a storage device for storing digital or analog data as measured by the electrodes 406 and 408. The memory 418 may be nonvolatile memory such as random access memory (RAM), flash memory, or a miniaturized hard drive. The A/D and peak detector 422 may be used to convert analog data measured from the heart 410 into digital signals for storage in the memory 418. The A/D and peak detector 422 may also be used to measure the peak amplitude of the heartbeat as recorded. The data may be converted from analog form to digital for ease of storage in the memory 418 or for easier or subsequent transmission to the receiver 402.

The electrode leads 406 and 408 may be attached in any number of locations within the heart. In particular, there are three main vascular beds in the heart 410. In some embodiments, the electrodes may be connected in two to four locations. By monitoring the heart in multiple sites, plus a reference point in the atrium of the heart 410, the monitor 400 may perform a more sensitive evaluation of the electrocardiographic changes in the signal amplitude and morphology or shape of the wave. The electrode leads 406 and 408 allow for a more accurate reading than an endomyocardial biopsy. In one example, the left lead, electrode lead 408, may be placed via the coronary sinus.

Various amplifiers 430, and 432 are required for the electrodes 406 and 408 of the heart monitor 404. Each amplifier may detect unipolar myocardial signals from the screw-in or transvenous electrode leads 406 and 408 placed in either the atrium or ventricle. The processor 420 may switch the amplifiers to sequentially record the signal amplitudes using the A/D and peak detector 422. The maximum and minimum amplitudes recorded in any given period of time, such as every four hours, eight hours, or twenty four hours are used to obtain an average amplitude value. The average amplitude may also be determined for each activity level.

The amplifiers 426, 428, 430, 432, and 434 are used for the heart monitor 404 and may have a band pass characteristic for the different signals that may be detected, monitored, recorded and stored. For example, an external transient event recorder (ETER) may have a band pass filter centered at approximately 28 Hz. This band pass is sensitive to varying cardiac rhythms as measured by the heart monitor 404. The narrow band pass filter reduces baseline drift as the patient moves.

If the monitor is monitoring an electrocardiogram signal (ECG), the center frequency may be approximately 80 Hz. This amplifier and filter is sensitive to baseline changes or drift due to motion and would require a correction algorithm be performed for the monitored signal by the processor 420. For an IRAM monitor, the center frequency would be approximately 200 Hz which is required to detect the signals that have been identified to change during heart rejection.

The piezoelectric accelerometer 436 may be a three axis piezoelectric sensor that determines both the position and activity level of the patient at any given time. The piezoelectric accelerometer 436 determines the activity level of the patient by converting the motions of the patient into an electrical signal that may be filtered or amplified by the amplifier 434 to generate a signal that may be used by the processor 420 to determine the activity level for storage in the memory 418. The piezoelectric accelerometer 436 may be used to initiate the recording of data by the electrodes 406 and 408.

In another embodiment, the piezoelectric accelerometer 436 may be used as an acoustic microphone to listen for lung sounds. For example, the piezoelectric accelerometer 436 may be used to determine whether a patient has pulmonary edema, mitral stenosis, pulmonary congestion, pneumonia, or other lung problems. The previously described library may also include lung related sounds for determining whether the piezoelectric accelerometer 436 has determined a lung issue that may need to be reported to the doctor.

The piezoelectric accelerometers 438 and 440 may detect acceleration in one or more directions. In one embodiment, the piezoelectric accelerometers 438 and 440 may be unidirectional accelerometers for measuring the motion of the different parts of the heart 410. The piezoelectric accelerometers 438 and 440 are positioned within the electrode leads in order to best sense the motion of the heart 410. The piezoelectric accelerometers 438 and 440 may also be used to measure not only the occurrence of a heart contraction, but the force of the heart contractions as well.

The telemetry circuitry 414 is the circuitry used to wirelessly transmit data to the receiver 402. The telemetry circuitry 414 may use any number of wireless protocols to send the data to the receiver 402. Telemetry protocols may include any number of RF signals including Bluetooth, WiFi, a specialized medical signal, and other protocols using low power signals. The telemetry circuitry 414 may include a transmitter and in some cases a receiver for receiving verification that the recorded data has been received by the receiver 402. During the time that the telemetry circuitry transmits data to the receiver 402, the processor 420 may disable the amplifiers 426, 428, 430, 432, and 434 for a short period of time in order to conserve power and ensure that the data transmission does not interfere with the detection of cardiac signals. The telemetry circuitry 414 may terminate sending or retrying to send data once a handshake or confirmation signal is received from the receiver 402.

In another embodiment, the telemetry circuitry 414 may use radio frequency identification (RFID). For example, the telemetry circuitry 414 may only be activated when in proximity to the receiver 402. The receiver 402 may temporarily power and receive data from the heart monitor 404 by transmitting a power signal similar to the use of RFID tags.

The magnetic reed switch 412 may be used to manually activate the heart monitor 404 to send the recorded data. The magnetic reed switch 412 may be activated by placing an activation magnet over the monitor. The magnetic reed switch 412 may be any variety of magnetically sensitive semiconductor elements. For example, if the patient has experienced a heart event, the patient may use a magnet to activate the magnetic reed switch 412 to send the recorded data from the telemetry circuitry 414 to the receiver 402.

Figure 5:
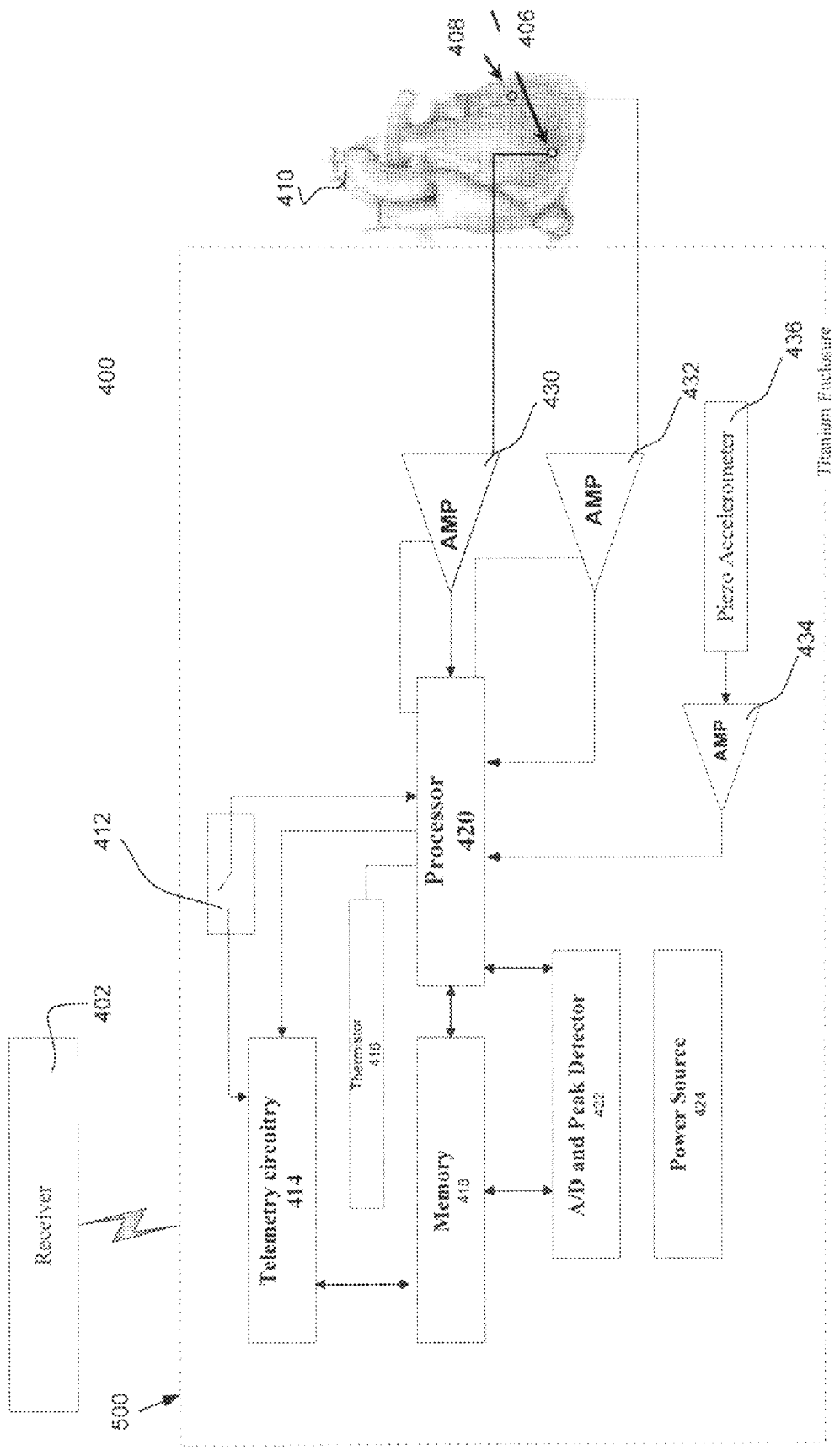
FIG. 5 is an alternative embodiment of a monitor system in accordance with the illustrative embodiments of the present invention.

FIG. 5 is an alternative embodiment of a monitor system in accordance with the illustrative embodiments of the present invention. Monitor 500 includes most of the elements described in FIG. 4 with a few exceptions. In monitor 500, the electrodes 406 and 408 do not include piezoelectric accelerometers and as a result there is no need for additional amplifiers. For example, the monitor 500 may be an internal transient event recorder (ITER) for recording heart events and subsequently notifying the doctor and/or patient through the receiver 402.

In monitor 500, the electrode lead 406 may be placed in the right atrial appendage for detecting near field P waves and far field R waves. Alternatively, the electrode lead 406 may be placed in the right atrial appendage for detecting P waves and the electrode lead 408 may be placed in the right ventricle for detecting R waves independently.

Figure 6:
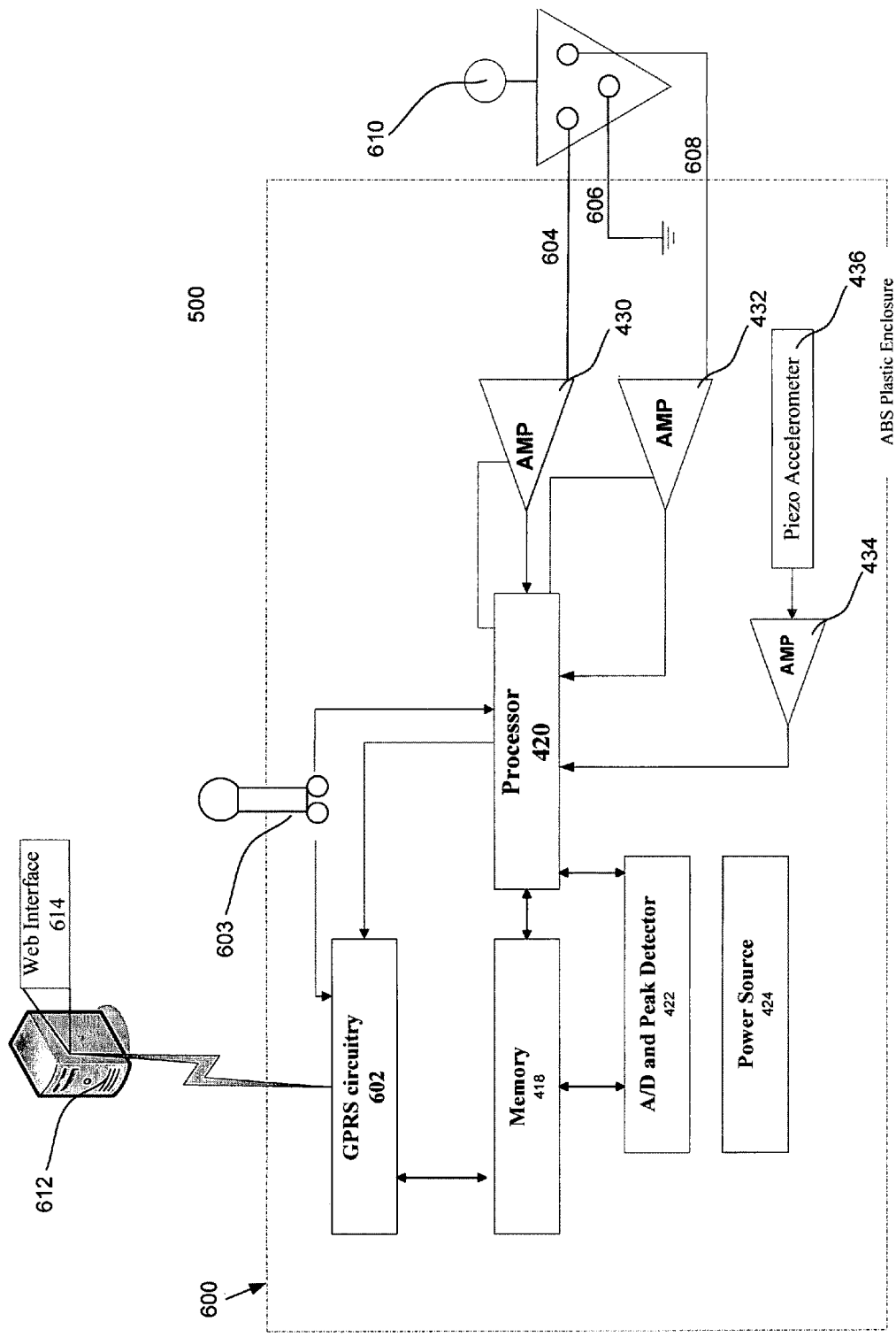
FIG. 6 is an embodiment of an external monitor system in accordance with the illustrative embodiments of the present invention.

FIG. 6 is an embodiment of an external monitor system in accordance with the illustrative embodiments of the present invention. External monitor 600 may include many of the elements previously described for FIGS. 5 and 6. The external monitor 600 further includes GPRS circuitry 602, button 603, and electrocardiogram electrodes 604, 606, and 608. In addition, the health monitor system of FIG. 6 includes patient 610, GPRS server 612, and web interface 614. The external monitor 600 may be worn or attached to the patient 610 in any number of ways. For example, the external monitor 600 may be worn on the patient's belt for convenience and easy access.

The ECG electrodes 604, 606, and 608 are attached to the patient 610 in the traditional manner. In one embodiment, once a heart event or other important data is recorded by the external monitor, the GPRS circuitry 602 may automatically transmit the data to the GPRS server 612 using the GPRS protocol. The GPRS circuitry includes the software and hardware necessary to send and receive data using GPRS. The doctor, patient, or other user may be provided access to the web interface 614 to review the monitored heart data. The web interface 614 may require that the GPRS server 612 be provided a password, authentication, or other security element for ensuring that the patient's data is only accessible by authorized parties. In one embodiment, the GPRS server 612 may automatically send an alert, email, or other message to the doctor, patient, or other user indicating that the external monitor 600 has recorded and transmitted heart event data.

Alternatively, the patient, upon feeling a symptom believed to be heart related, may activate the button 603. Once asserted, the button 603 sends a transmit signal to the GPRS circuitry 602 that automatically transmits the heart event data recorded by the external monitor and corresponding ECG electrodes 604, 606, and 608 to the GPRS server 612 indicating that this transmitted data was associated with a symptom. The power source 424 of the external monitor 600 may be rechargeable so that the patient may easily charge the external monitor 600 at night or add new batteries as needed. For example, the patient 610 may place the external monitor 600 in a charging cradle at night for mobile use during the day, much like a cellular phone or, if separate rechargeable batteries are used, replace the batteries in the device with fully recharged batteries and place the depleted batteries into the battery charger.

Figure 7:
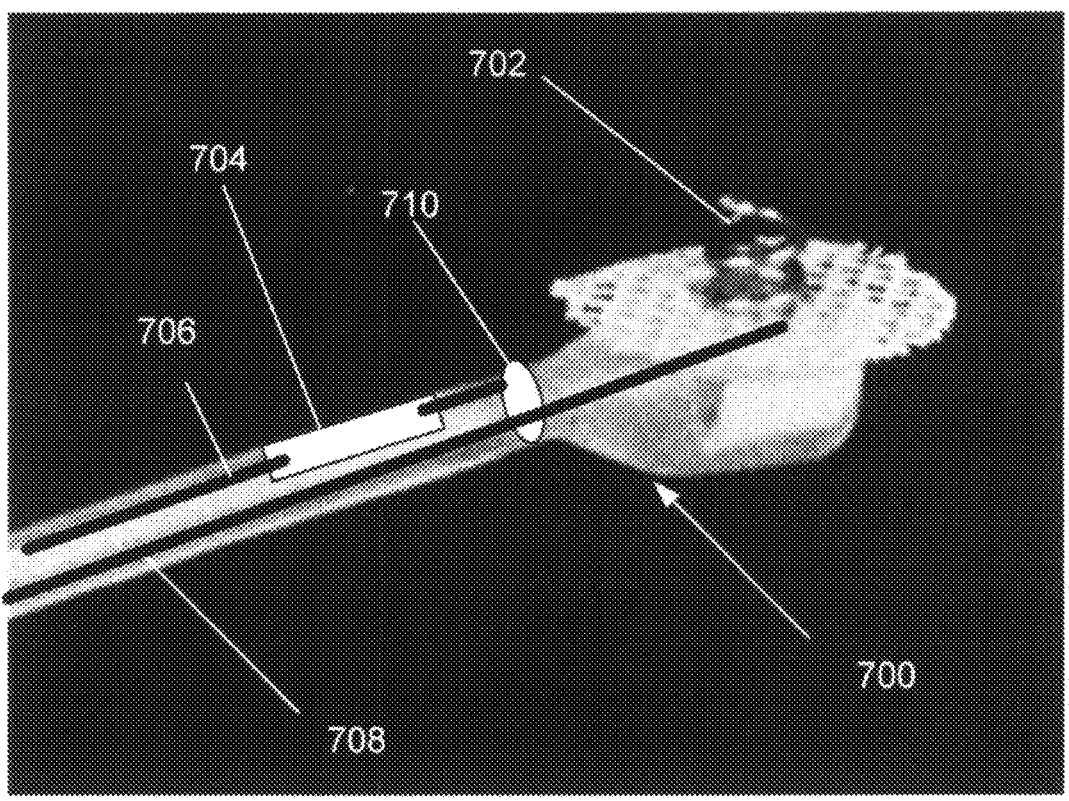
FIG. 7 is an example of a screw-in myocardial electrode lead in accordance with the illustrative embodiments of the present invention.

FIG. 7 is an example of a screw-in myocardial electrode lead in accordance with the illustrative embodiments of the present invention. An electrode lead 700 includes various elements including a screw-in tip 702, a piezoelectric accelerometer 704, wires 706, 708, and an electrode 710. The electrode lead 700 is a particular implementation of the electrode leads 406 and 408 of FIG. 4. The heart monitor preferably includes two electrode leads with one of the leads placed such that both right ventricular contractions and right ventricular depolarization signals may be detected. The second lead is preferably positioned such that both left ventricular contractions and left ventricular depolarization signals may be detected. However, any number of lead configurations may be used that allow both electrical and mechanical signals to be effectively received for monitoring.

The screw-in tip 702 is used to connect the electrode lead 700 to the muscle of the heart. The screw-in tip 702 may be attached myocardially or transvenously. Transvenous leads are passed into the heart via a vein and the screw tip is deployed after venous insertion. The electrode lead 700 may have an active fixation tip, such as the screw-in tip 702 or may include a passive fixation tip when placed transvenously.

The piezoelectric accelerometer 704 may be used to measure movement of the heart or alternatively may be used to measure the force of the contraction. The piezoelectric accelerometer 704 may be a variety of different sizes, thicknesses, shapes and metalization options.

As mentioned, the piezoelectric accelerometer 704 may be used as a microphone using a technique of acoustic cardiology. With acoustic cardiology, timing events are monitored using heart sounds, such as valve closure, which are a second order effect of the ventricles contracting. By using a piezoelectric sensor in the electrode lead 700, the monitor may record the primary indicator of ventricular contraction for determining the condition, strength, and relative performance of the heart.

The piezoelectric accelerometer 704 is connected to the monitor on one end and the electrode through the wire 706. The electrode 710 acts as a reference point to the piezoelectric accelerometer 704 and makes contact with body tissue. The voltage and current measurements recorded by the piezoelectric accelerometer 704 are passed to the monitor through wire 706. The wires 706 and 708 may be any transmission medium able to conduct signals received from the screw-in tip 702 and piezoelectric accelerometer 704 to the body of the monitor. In one embodiment, the piezoelectric accelerometer 704 is connected to an amplifier, such as amplifier 426 of FIG. 4 which is referenced to the titanium enclosure that is in contact with subcutaneous body tissue. The right ventricular screw-in lead tip 702 is connected to the amplifier 430 by the wire 706. The wire 708 passes-through the electrode 710 without making contact. For example, the electrode 710 may include an insulated pass-through by which the wire 708 continues without making electrically contacting the electrode 710. Amplifier 430 of FIG. 4 is also referenced to the titanium enclosure that is in contact with subcutaneous body tissue.

Thus, both the piezoelectric accelerometer 704 and the screw-in electrode 702 are connected to amplifiers referenced to the patient's subcutaneous tissue for measurement of both the mechanical movement of the right ventricle and the electrical depolarization signal or IMEG. A similar configuration for amplifiers 428 and 432 of FIG. 4 exists for the left ventricular electrode lead.

The use of electrode lead 700 is particularly useful for the monitor because of the ability to measure the contractile movement, contractile force, and timing of the contraction. The timing measurements are particularly useful when the two leads are attached to the left and right ventricle. The electrode lead 700 may also be used for cardiac pacing in the case where pacemaker functionality is integrated with the monitor.

FIG. 8 is a sample of heart data in accordance with the illustrative embodiments of the present invention. Table 800 includes various elements including an IRAM serial number 802, a patient number 804, a protocol 806, and a date 807. Various data may be recorded by electrode lead 1 808 and electrode lead 2 810. The data for electrode leads 1 and 2 808 and 810 includes a number of readings 812, IMEG amplitude 814, average IMEG average 816, IMEG amplitude 818, time 820, dV/dt 822, and average dV/dt 824.

Table 800 is an example and shows only two sets of monitored and recorded heartbeats for two, five minute intervals. The recorded data of table 800 may include any number of data sets. All or a portion of the data may be recorded and/or subsequently transmitted to the receiver. Also, the averages of all the averages may be made so that there is only one value for the average IMEG amplitude 816 and the average dV/dt 824.

Figure 9:
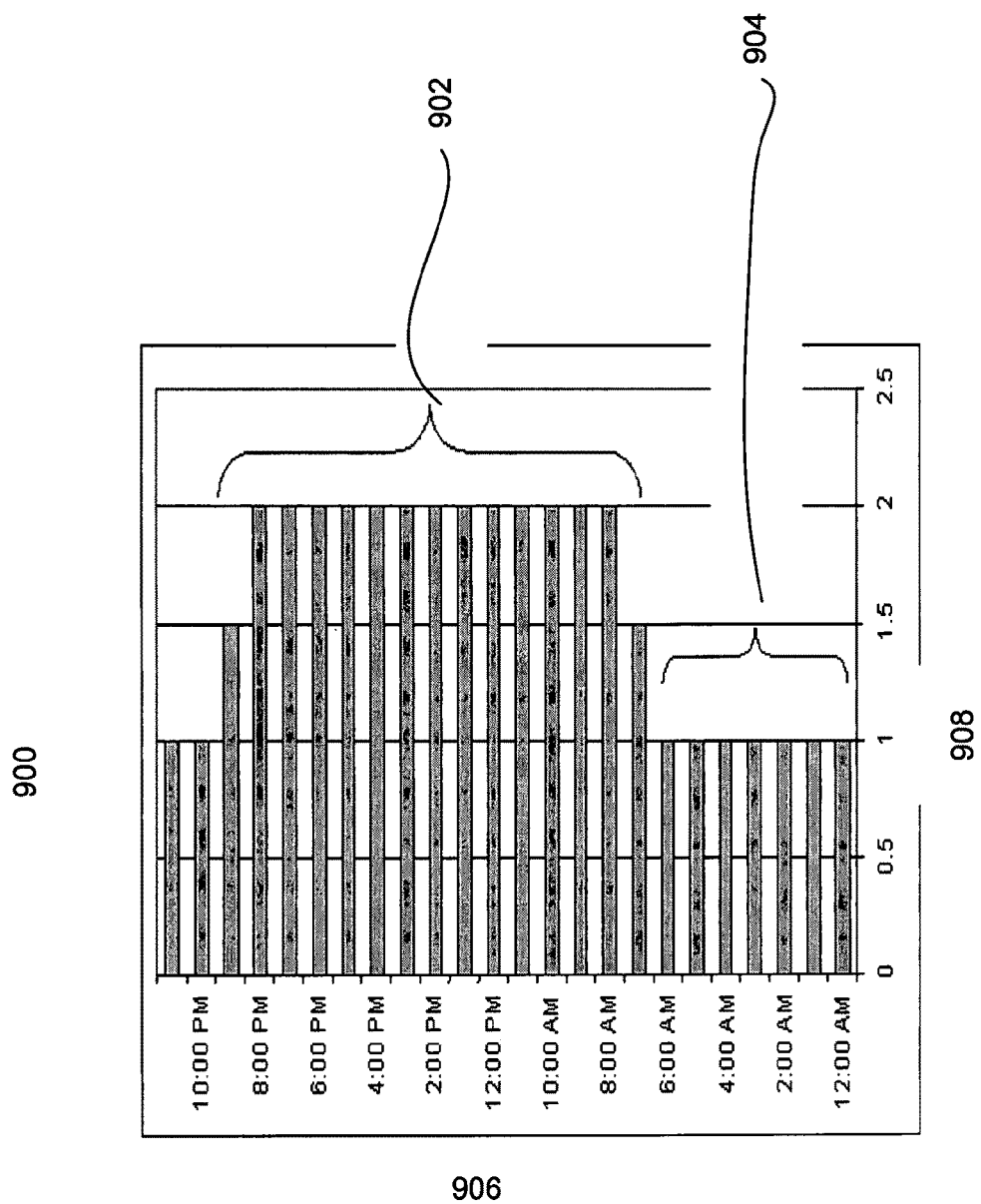
FIG. 9 is an illustrative graph of physical activity in accordance with the illustrative embodiments of the present invention.

FIG. 9 is an illustrative graph of physical activity in accordance with the illustrative embodiments of the present invention. Graph 900 includes various sections including section 902 and section 904. The x-axis represents physical activity level 906 and the y-axis represents time 908 throughout the day. Section 902 indicates increased physical activity levels as sensed by piezoelectric accelerometers in a monitor, such as monitor 104 of FIG. 1.

Section 902 indicates increased physical activity levels when the patient is awake and performing various activities. For example, the patient may be walking and performing the activities of the day. Section 904 indicates decreased activity levels when the patient is sleeping or profoundly resting. The assessment of various activity levels is made by monitoring the acceleration change in the piezoelectric accelerometer per unit time or dA/dt.

The monitor may be set to monitor only and/or monitor and record physical activity using a looping method to record events when the patient is awake and asleep or either awake only or asleep only. During the activity levels shown in 902 the monitor is not recording samples as described.

Section 904 indicates decreased activity levels when the patient is sleeping or profoundly resting. Once the reduced activity levels of section 904 are detected, the signals from the piezoelectric accelerometer may activate the monitor to record heart data while the patient is sleeping and to suspend recording when activity levels indicate the patient is awake as shown by section 902. This is extremely beneficial when used to monitor transplant patients for rejection since only monitoring of IMEG and dV/dt data during sleep is useful in detecting rejection.

Figure 10:
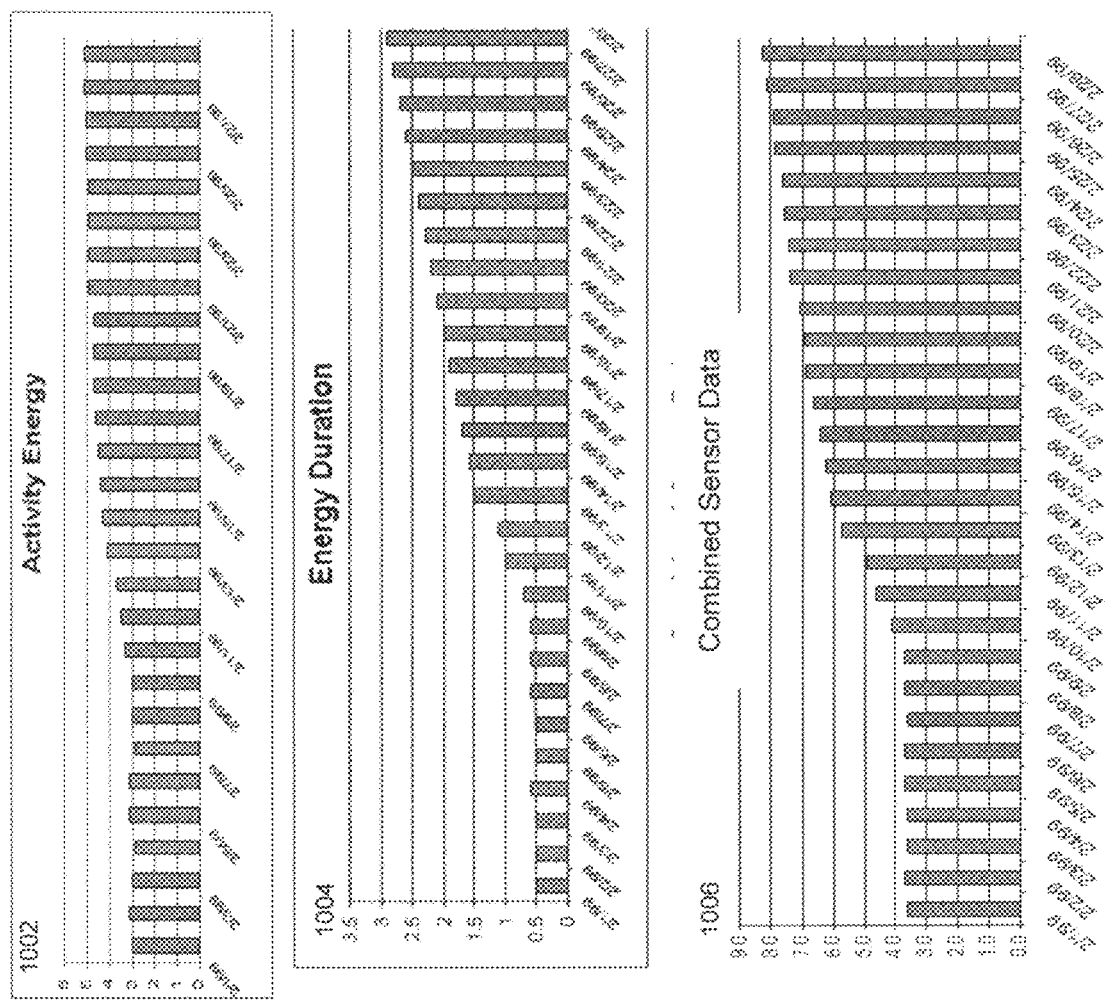
FIG. 10 is an example of data recorded by a monitor in accordance with the illustrative embodiments of the present invention.

FIG. 10 is an example of data recorded by a monitor in accordance with the illustrative embodiments of the present invention. FIG. 10 includes graph 1002, graph 1004, and graph 1006. Graphs 1002, 1004, and 1006 illustrate activity data that may be collected for a patient that is experiencing improving health. Graphs 1002, 1004, and 1006 may be displayed to a patient, doctor, or other specialist or user for graphically representing the progress of the patient. The graphs 1002, 1004, and 1006 may be part of a graphical user interface of a computing device or may be displayed independently. The person viewing the graphs 1002, 1004, and 1006 may specify values, parameters, or conditions for displaying the data. For example, the data may be shown for each hour of each day or for every other day as selected by the user.

Graph 1002 includes data for activity energy. The activity may be monitored by a piezoelectric accelerometer, such as piezoelectric accelerometer 436 of FIG. 4. The activity data is recorded by a monitor, such as monitor 104 of FIG. 1. As shown, graph 1002 indicates that the activity energy of the patient has been steadily increasing over time which may indicate that the health of the patient is improving.

Graph 1004 includes data for energy duration. Energy duration may specify the amount of time the monitor records the patient performing activity above a specified threshold. For example, any recorded activity level that does not include sleeping may be displayed in the graph 1004. As a result, the graph 1004 may specify the amount of time a patient is awake and active for determining the energy level of the patient.

Graph 1006 includes data for combined sensor data. Graph 1006 may be a combination of data and factors. For example, graph 1006 may include the data measurements as shown in graph 1002 and 1004. As a result, a doctor may more easily evaluate the condition of the patient based on the activity levels performed by the patient and the amount of the time the patient spends performing that activity.

FIG. 11 is an example of data recorded by a monitor in accordance with the illustrative embodiments of the present invention. FIG. 11 includes graph 1102, graph 1104, and table 1106 similar to those of FIG. 10. Graphs 1102, 1104, and table 1106 illustrate activity data that may also be collected for a patient that is experiencing improving health.

The graph 1102 indicates the activity duration. Graph 1102 may indicate the amount of time the monitor records the patient active at one or more activity levels as measured per hour, day, week, month or year. For example, graph 1104 may display the amount of time the patient engages in significant activity each day. Graph 1104 may specify the energy duration for one or more activity levels as selected by the user.

The graph 1104 is an indirect assessment of physiological status. The indirect assessment of physiological status may include a number of values or factors. The graph 1104 may include data that is scaled, averaged, or otherwise mathematically manipulated to provide a graphical representation, such as a bar chart, of the overall health of the patient. For example, graph 1104 may include an average for all recorded activity levels and the duration the patient is active in that activity level as well as a factor for sleep.

Table 1106 may include any number of data values measured by the monitor. Table 1106 may show data as recorded for each day. Table 1106 may include data values for activity (reciprocal of sleep), the activity threshold or exercise level, and the activity duration or time of exercise. This data may be added to form a total that may be used for a doctor in measuring all activity parameters for a patient in order to obtain a more sensitive and specific evaluation of a patient's overall health status.

Figure 12:
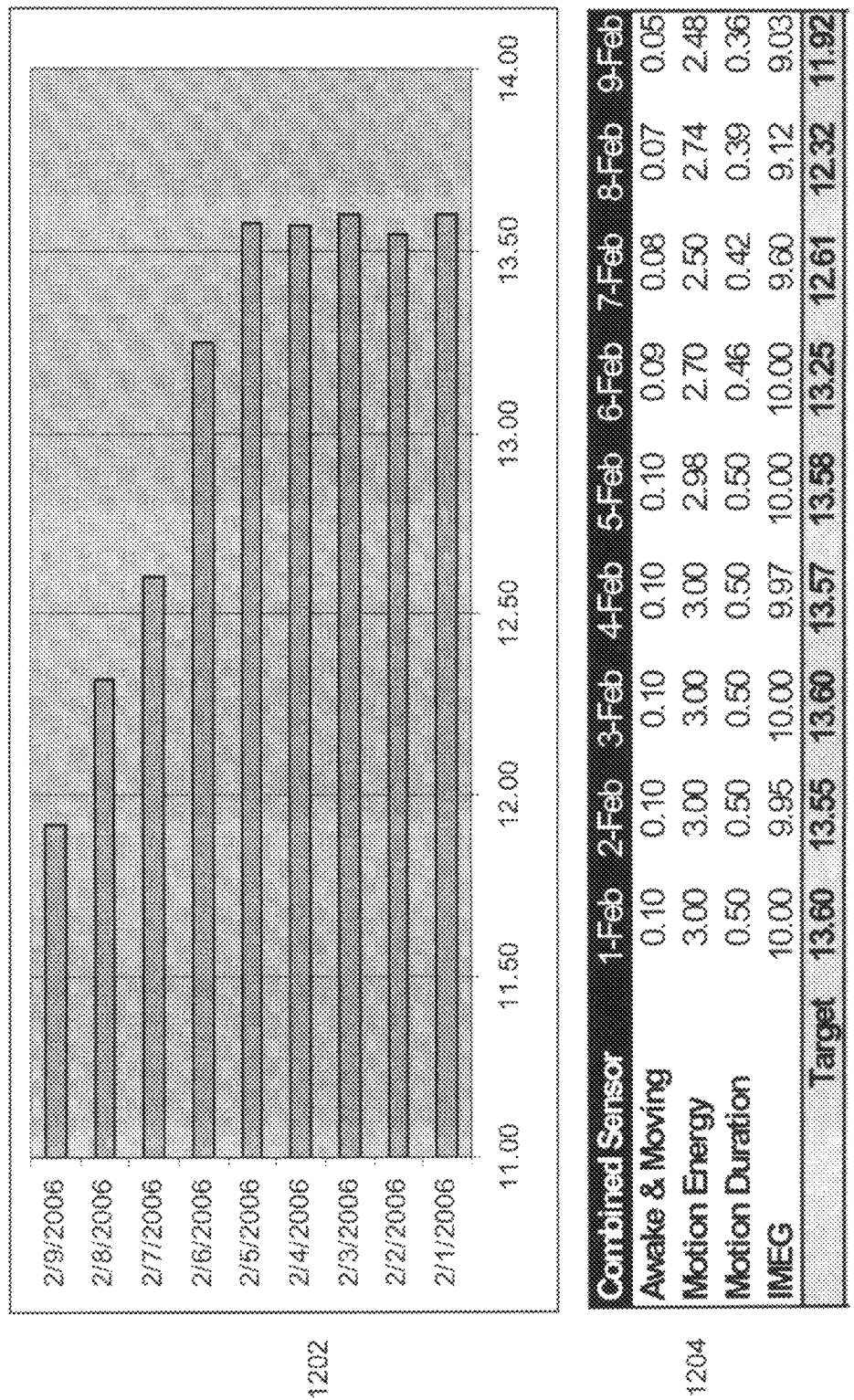
FIG. 12 is an example of data recorded by a monitor in accordance with the illustrative embodiments of the present invention.

FIG. 12 is an example of data recorded by a monitor in accordance with the illustrative embodiments of the present invention. FIG. 12 includes graph 1202 and table 1204. 1202 may indicate the target or overall health level of the patient. Table 1204 illustrates data that may be measured and recorded to generate graph 1202. Graph 1202 and table 1204 suggest that the patient's health status is deteriorating.

Figure 13:
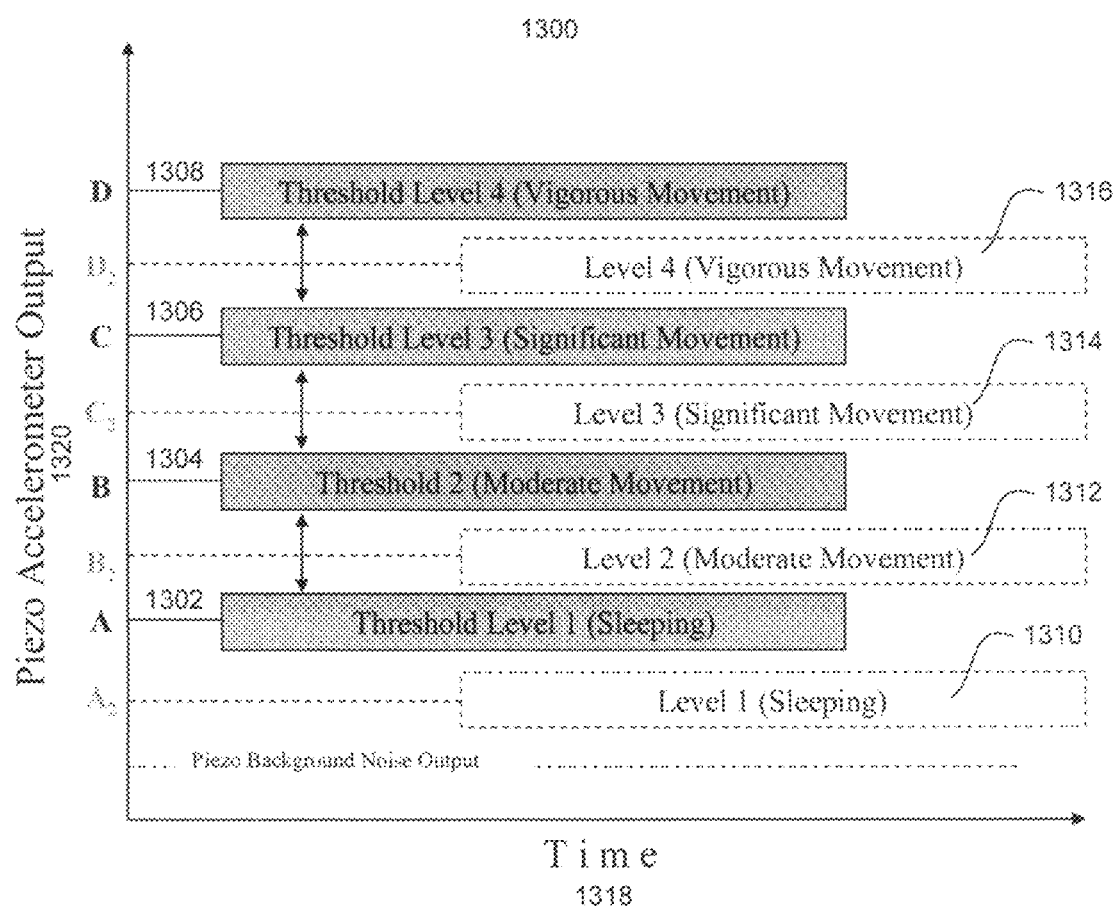
FIG. 13 is a graphical illustration of threshold levels in accordance with the illustrative embodiments of the present invention.

FIG. 13 is a graphical illustration of threshold levels in accordance with the illustrative embodiments of the present invention. The monitor previously described may be constantly monitoring and recording data or may only record data that is above a specified threshold. The threshold may be a specified activity level as measured by the monitor, piezoelectric accelerometers, or both. Graph 1300 illustrates various threshold levels including threshold A 1302, threshold B 1304, threshold C 1306, and threshold level D 1308. The thresholds level 1 1310, level 2 1312, level 3 1314, and level 4 1316 are represented by dotted lines as shown. The x-axis 1318 of the graph 1300 represents time and the y-axis 1320 of the graph represents piezoelectric accelerometer output. The piezoelectric accelerometer output may be measured by one or more piezoelectric accelerometers or a multi-axis accelerometer in the body of a heart monitor, such as monitor 104 of FIG. 1. The piezoelectric accelerometer output of the y-axis 1320 may be represented by a voltage that indicates the level of energy that the patient is imparting to his/her motions. The monitor may record the activities of the patient throughout the day and data corresponding to the activity level and duration of time the patient spent at that activity level.

Levels 1-4 1310, 1312, 1314, and 1316 represent the automatically self-adjusting settings for activity threshold. For example, when the patient is home after surgery and spends several days in bed recovering from an illness, surgery, etc., the auto-threshold level may decrease until the patient begins the recovery process.

Figure 14:
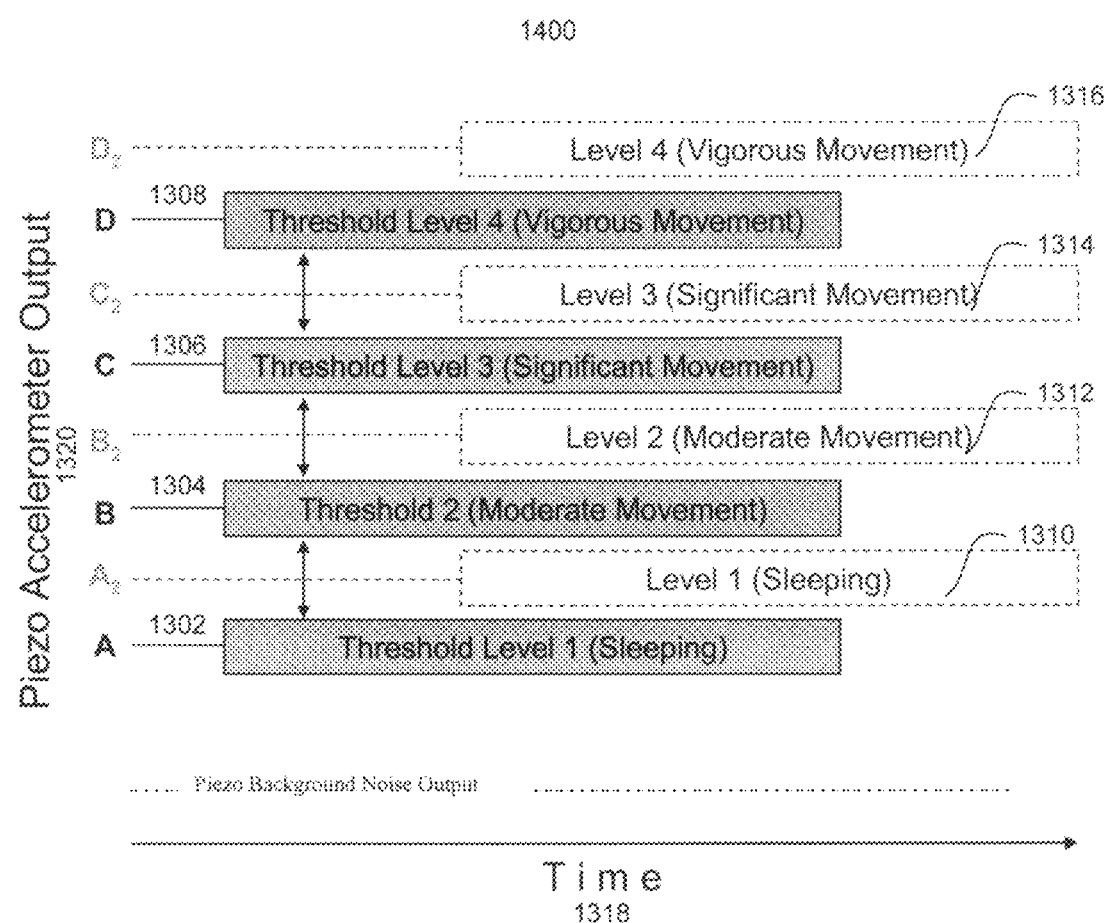
FIG. 14 is a graphical illustration of adjusted threshold levels in accordance with the illustrative embodiments of the present invention.

FIG. 14 is a graphical illustration of threshold levels in accordance with the illustrative embodiments of the present invention. The Levels 1-4 1310, 1312, 1314, and 1316 have been auto-adjusted based on the recent activity of the patient recovering from an illness. As a result, the graph 1300 shows automatically self-adjusting threshold levels A-D 1302, 1304, 1306, and 1308 as the patient begins to improve and increases his/her activity level.

As shown in graph 300 of 13B, the Levels 1-4 1310, 1312, 1314, and 1316 have all automatically increased above the next threshold level. The adjustment shown in graph 300 illustrates the categorization of activity into different activity levels based on trends and patient history. In one embodiment, the auto-adjustment of the levels 1-4 1310, 1312, 1314, and 1316 may be performed by the monitor. The space, voltage or y-axis 1320 between levels 1-4 1310, 1312, 1314, and 1316 are not necessarily linear. Statistical analysis may be used to auto-set the different threshold levels A-D 1302, 1304, 1306, and 1308 in order to characterize different activity measurements into the corresponding levels 1-4 1310, 1312, 1314, and 1316. The Levels 1-4, 1310, 1312, 1314, and 1316 may also be auto-adjusted downward if the patient suffers a recovery relapse or other setback that affects the activity level measured by the monitor. For example, if the patient is recovering from an illness, the patient is less likely to spend time sleeping or resting when recovering is progressing as it should.

Figure 15:
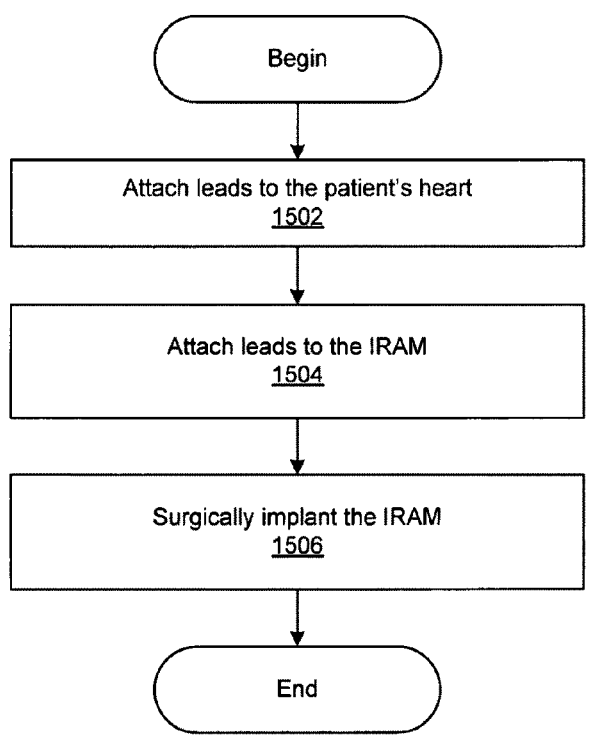
FIG. 15 is a flowchart for a process for inserting a heart monitoring device in accordance with the illustrative embodiments of the present invention.

FIG. 15 is a flowchart for a process for inserting a heart monitoring device in accordance with the illustrative embodiments of the present invention. The process of FIG. 15 may be implemented for a transplant patient or other patient that needs physiological or heart monitoring. The process of FIG. 15 may be implemented by a surgeon, cardiologist or other medical technology specialist. The process of FIG. 15 allows an intramyocardial electrogram to be taken using myocardial leads or transvenous leads.

The process of FIG. 15 begins, after the patient is medically prepped and anesthetized, as with most surgical procedures, by attaching the leads to the patient's heart (step 1502). The electrodes or leads may be pacemaker style electrode leads or modified pacemaker style electrode leads containing piezoelectric sensors for measuring both the electrical and mechanical activity of the heart. In one embodiment, the leads may be myocardial screw-in leads typically used for pacemaker applications that are designed to screw into the myocardial wall of the heart much like a corkscrew. In another embodiment, the leads may be inserted transvenously. A transvenous lead would be passed through a vein to the right ventricle. An incision in the deltoid-pectoral groove in the upper left or right chest area may be used to find a vein in order to insert the transvenous lead rather than inserting the leads into the heart using a thoracotomy or other extremely invasive and dangerous procedure.

The transvenous lead may still have a screw tip, but the screw is retracted into the body of the lead. Once the lead is passed transvenously to the right ventricle, the back end of the lead connector may be rotated to deploy a corkscrew tip if the lead is an active fixation design or it may be a passive fixation element whereby the lead is wedged into the trabeculae carne.

The two leads may be inserted into the right ventricle. One lead is inserted for contact to the right ventricular septum, which is the wall separating the right ventricle from the left ventricle. The right ventricular septum is anatomically part of the left ventricle and sensing of its mechanical movement may be detectable with a piezoelectric equipped electrode lead. The other lead is inserted into the apex of the right ventricle or the right lateral wall for measuring the right ventricle.

Next, the surgeon attaches the leads to the implantable rejection assessment monitor (IRAM). The surgeon further surgically implants the IRAM (step 1506) with the process terminating thereafter. The IRAM may be securely implanted in a subcutaneous pocket of the abdomen or in the deltoid-pectoral area of the shoulder. The surgical procedure may be performed in a hospital catheterization laboratory or a special procedures room typically with the patient usually under local anesthetic.

Figure 16:
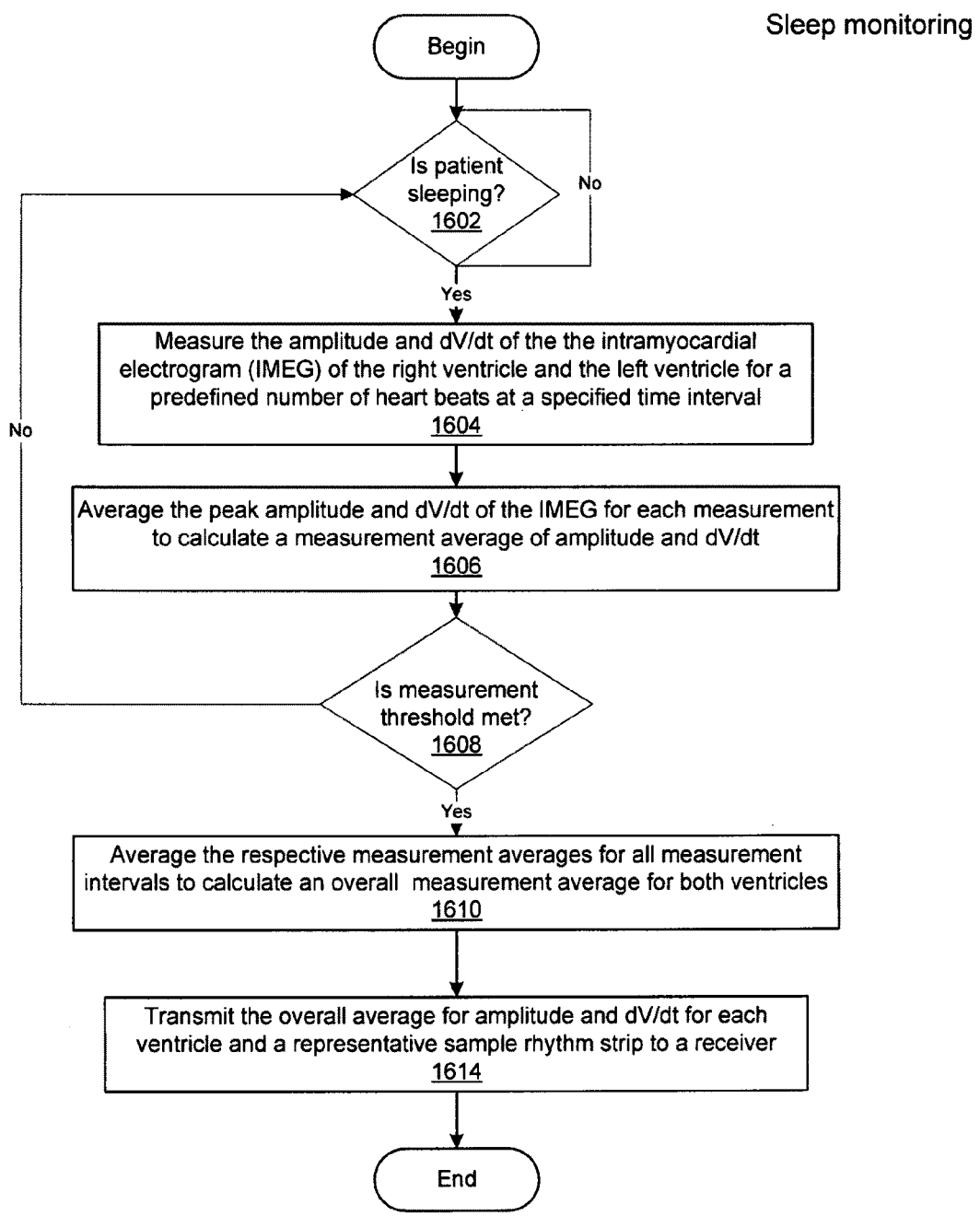
FIG. 16 is a flowchart of a process for performing heart monitoring during sleep in accordance with the illustrative embodiments of the present invention.

FIG. 16 is a flowchart of a process for performing heart monitoring during sleep in accordance with the illustrative embodiments of the present invention. The process of FIG. 16 may be performed by the IRAM or heart/physiological status monitor referred to hereinafter as the monitor after having been surgically implanted.

The process begins with the monitor determining whether the patient is sleeping (step 1602). The determination of step 1602 is made in order to take readings and measurements of the heart. Ideally, the best time to take measurements for transplant rejection is during alpha sleep or the sleep before rapid eye movement (REM) sleep begins. During the first few hours of sleep, the user is most likely to have a steady heart rate, reduced emotional stress, and other factors that make measurements taken at that time the most accurate for determining heart and physiological status.

The process of FIG. 16 continuously verifies whether the patient is sleeping in order to ensure the uniformity of data. For example, if the monitor determines that the patient is not asleep in step 1602, the measurements of any data go on hold until the patient is asleep again. This provides uniform data that may be statistically analyzed over time. As a result, measurements of the heart are performed more reliably with greater effectiveness for a real world environment where the patient is sleeping and most comfortable.

The determination that the patient is asleep may be made in any number of ways and using a combination of information and data. In one embodiment, the monitor and specifically piezoelectric accelerometers within the monitor may determine the physical position of the patient. The patient is more likely to be sleeping when positioned horizontally or reclined. The monitor may also use the heart rate of the patient to determine whether the patient is active or resting. For example, even though the patient is partially reclined in a reclining chair the patient may be watching an action movie that has stimulated emotional stress so that adrenaline causes his heart to pump faster than normal. Even though reclined, this is not an ideal time to take heart measurements. The monitor may also use previous patterns to use existing data and historic data to determine when the patient is sleeping. In yet another embodiment, the piezoelectric sensor within the monitor may be used to determine that the patient is sleeping by monitoring the activity variance or dA/dt, where dA/dt is a change in activity per unit time. Little or no activity variance is a good indicator that the patient is sleeping If the patient is not sleeping, step 1602 is repeated until the monitor determines that the patient is asleep. Once the patient is determined to be asleep in step 1602, the monitor measures the amplitude and dV/dt of the intramyocardial electrogram (IMEG) of the right ventricle and left ventricle for a predefined number of heartbeats at a specified time interval (step 1604). The measurements of the left and right ventricle for amplitude and dV/dt may be made individually or simultaneously. In one example, the monitor may have a predefined number of ten heartbeats to evaluate and a specified time interval to view ten heartbeats every five minutes. As a result, the monitor records ten heartbeats every five minutes for amplitude and dV/dt for each ventricle or lead. In some patients, the heart rate is naturally elevated because of transplant, drugs or other factors. Measurements for the predefined number of heartbeats may be measured much faster because of their naturally faster heart rate.

The monitor averages the peak amplitude and dV/dt of the IMEG for each measurement to calculate a measurement average of amplitude and dV/dt (step 1606). By taking a running average, the monitor is able to accurately monitor heart statistics while minimizing the values that must be stored in memory. As a result, the monitor may take a very large sample size each night or each time the patient sleeps for providing the patient's doctor important information regarding heart and physiological status.

The monitor determines whether the measurement threshold is met (step 1608). The measurement threshold is a specified number of measurements or samples. The measurement threshold may be set by default or may be communicated to the monitor by the patient's doctor based on circumstances and need. For example, the measurement threshold may be thirty six samples for each ventricle and based on twelve measurements per hour for three hours.

If the measurement threshold is not met, the monitor determines whether the patient is sleeping (step 1602). If the monitor determines the measurement threshold is met in step 1608, the monitor averages the respective measurement averages for all measurement intervals to calculate an overall measurement average for both ventricles (step 1612). The overall average is a single number for amplitude and dV/dt for each ventricle. In another embodiment, the overall average of step 1612 may be a single number for the entire heart for amplitude and dV/dt.

Next, the monitor transmits the overall average for amplitude and dV/dt for each ventricle and a representative sample rhythm IMEG or electrocardiogram (ECG) strip to a receiver (step 1614) with the process terminating thereafter. The data may be transmitted in a number of different ways. In one embodiment, the data may be transmitted at a predetermined time, such as 7:00 a.m. every morning. In another embodiment, the overall averages may be transmitted to the receiver at any time the monitor detects the presence of the receiver for transmission. In yet another embodiment, the overall averages may be transmitted to the receiver when the patient awakes from sleep evidenced by an increase in the monitored activity variance, dA/dt. The receiver may be a unit that is connected to a communications line, such as an Internet connection or a modem for sending data to a data processing system, server, or other computing platform for access by the doctor. In another embodiment, the patient may wear the receiver on a belt or harness and may use wireless technology, such as general packet radio service (GPRS) to transmit the data to a data processing system, server, or other computing platform for access by the doctor. The receiver may also be a specially programmed cellular phone designated to send and receive data from the monitor.

The representative sample is one entire sample measurement that is recorded by the monitor. The representative sample illustrates the entire heartbeat wave form for analysis and understanding of the condition of the patient's heart. For example, the representative sample may show a ten beat pattern for both the left and right ventricle. The representative sample transmitted during step 1614 allows a doctor or other specialist to see what is happening with the heart in order to perform other analysis or determinations. The representative sample also indicates the quality of the signal being received by the monitor ensuring that the monitor is working properly and that the electrodes are still properly connected.

The monitor may also be configured to continuously watch for a heart event, such as arrhythmias, trigeminy, bradycardia, tachycardia, and premature ventricular contractions (PVC). When an event is detected, the monitor may immediately transmit the information to the receiver for transmission and subsequent analysis by the doctor. The monitor may also transmit based on a predefined time period or other preferences.

Figure 17:
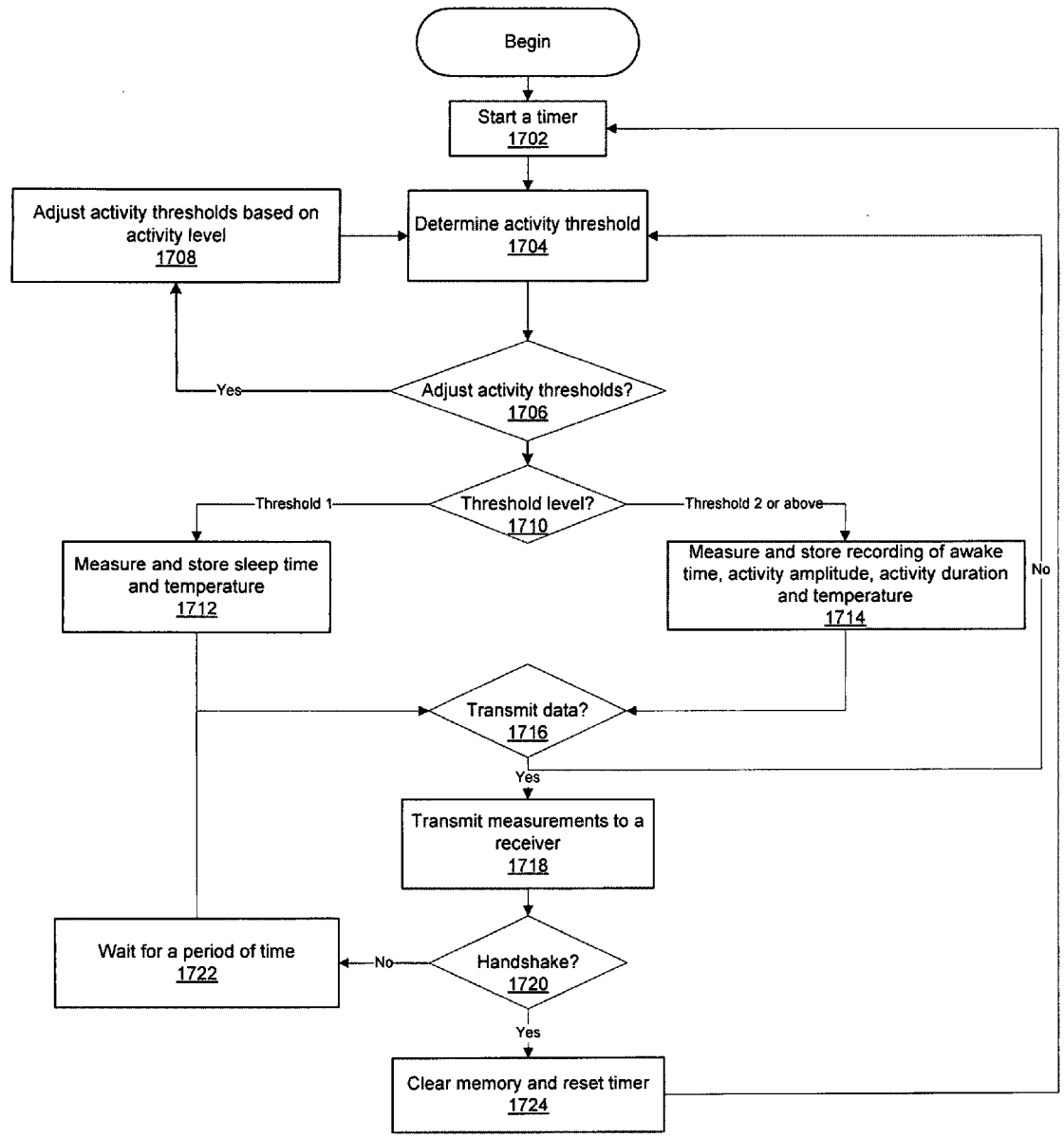
FIG. 17 is a flowchart of a process for measuring activity levels in accordance with the illustrative embodiments of the present invention.

FIG. 17 is a flowchart of a process for measuring activity levels in accordance with the illustrative embodiments of the present invention. The process of FIG. 17 may be implemented by a heart monitor or physiological status monitor. The process of FIG. 17 begins by starting a timer (step 1702). The timer ensures that the monitor transmits information or a status report once a day regardless of the sleeping activity of the patient.

The monitor then determines an activity threshold (step 1704). The activity threshold may be determined using various information and factors. The activity threshold may indicate the current activity level of the patient. The activity level indicates the amount of energy detected by the piezoelectric sensors in the monitor imparted by the patient's movements. In one embodiment, the activity level is determined by piezoelectric accelerometers within the monitor that specify the level of movements being performed. The thresholds are based on the output of the accelerometer which may be a voltage, other digital signal, or analog signal. There may be any number of activity thresholds, tiers, or ranges that indicate a specified activity level.

In one embodiment, there are four thresholds, any activity less than the first threshold indicates that the patient is asleep. Activity above the first threshold, but below the second threshold, indicates the patient is performing moderate movement. Activity above the second threshold, but below the third threshold, indicates that the patient is performing significant movement. Activity above the third threshold, but below the fourth threshold, indicates that the patient is performing vigorous movement. All activity for the patient throughout the day may be categorized into one of the threshold levels. The activity thresholds specify a categorization for each activity level. In another example, the activity level may be determined based on the heart rate of the patient and the activity as determined by the piezoelectric accelerometer.

The monitor determines whether to adjust the activity thresholds (step 1706). The determination to adjust the activity threshold may be made on past data trends or based on new activity levels. For example, if the patient has recently been performing vigorous movement, the threshold level may be higher than if the patient was relatively sedentary. Some patients may never reach the point of performing vigorous movement. As a result, the threshold levels are automatically set and modified based on the measured activity of the patient. The determination of step 1706 may be made by a processor, logic, memory, and piezoelectric sensors within the monitor. The initial threshold ranges or values may be set arbitrarily or based on values determined for previous patients with similar circumstances.

If the monitor determines to adjust the activity threshold, then the monitor adjusts the activity thresholds based on the activity level (step 1708). Different patients may have different threshold levels. For example, many patients are naturally very active and may have higher threshold levels whereas other users are by nature much more sedentary or inactive. In another example, the active patient may get very sick or undergo a transplant necessitating an adjustment of the activity thresholds as the patient recovers and slowly returns to a more active lifestyle. The activity threshold is auto-set by the monitor based on actual patient activity measured by the monitor as objectively measured by one or more piezoelectric accelerometers. Next, the monitor determines the activity threshold (step 1704).

If the monitor determines not to adjust the activity threshold in step 1706, then the monitor determines whether the threshold level is one or below or two or above (step 1710). If the threshold is at one, the monitor measures and stores the sleep time and temperature (step 1712).

If the monitor determines the threshold is two or above, the monitor measures and stores a recording of time awake, activity amplitude, activity duration, and temperature (step 1714). By measuring and storing activity level measurements it is easy to see whether a patient is improving, getting worse, or stable with regard to physical activity. As a result, a doctor may objectively categorize a person's health based on activity. The data stored by the monitor is particularly suitable for graphing activity levels over time. The time awake indicates whether the patient is sleeping enough and active during the day. The activity amplitude and duration indicate what activity level is being reached and for how long.

After steps 1712 and 1714, the monitor determines whether to transmit data (step 1716). In one embodiment, the monitor may not transmit the data until the timer has reached a specified value or range. The determination may be made based on availability of the receiver, amount of stored information, or other factors. If the monitor determines not to transmit data in step 1716, the monitor determines the activity threshold (step 1704).

If the monitor determines to transmit data in step 1716, the monitor transmits measurements to a receiver (step 1718). The receiver may be a hardwired unit that is connected to a communication line. Alternatively, the receiver may be worn by the patient and may use wireless technology to broadcast the recorded data to a specified device, interface, portal, server, or recipient. Next, the monitor determines whether there is a handshake (step 1720). The handshake indicates whether the information was properly received. For example, the handshake may be received from a transceiver if the data transmitted from the monitor is received without errors. The handshake may be a confirmation or other signal indicating the data has been successfully received. If there is not a handshake, the monitor waits for a period of time (step 1720) and determines whether to transmit the data (step 1716).

If the monitor determines there is handshake in step 1720, the monitor clears the memory and resets the timer (step 1724). The memory is cleared to make space for new data. The reset timer indicates that data has been transmitted for that day or other specified time period and is reset to begin again. The monitor starts the timer (step 1702). The process of FIG. 17 is repeated continuously to monitor the status of the patient. As a result, doctors or other medical personnel may use the data measured and stored in steps 1712 and 1714 to determine the type of activity the patient is engaging in and how often the activity level is performed. The doctor may use previously recorded data to view changes in the patient's activity that are a direct byproduct of health and well-being. For example, during a patient/doctor visit, the doctor may say "let's pull up your data from last month and see how you are doing." The doctor may recommend new activities, drugs, or perform additional analysis based on information from the patient and the recorded data. For example, the patient may imply that he has been exercising, but the monitor may give a more realistic or accurate report of activity levels. The recorded data transmitted to the doctor provides an indirect measurement of cardiac performance, neurological, and physiological performance. The monitor is useful for patients that experience inactivity, over activity, or other combinations of activity problems.

Figure 18:
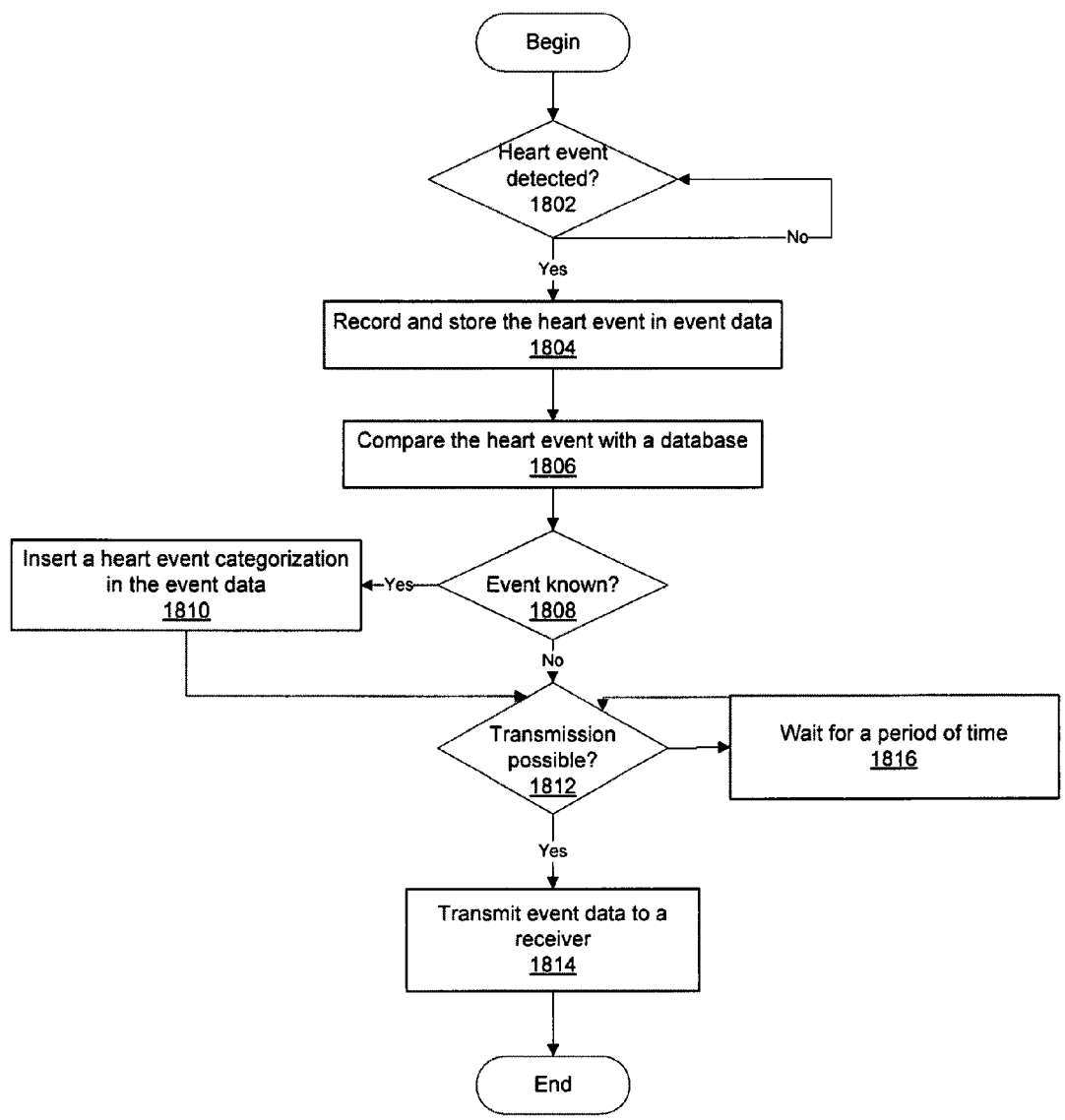
FIG. 18 is a flowchart of a process for detecting heart events in accordance with the illustrative embodiments of the present invention.

FIG. 18 is a flowchart of a process for detecting heart events in accordance with the illustrative embodiments of the present invention. The process of FIG. 18 may be implemented by a heart monitor or physiological status monitor. The process begins with the monitor determining whether a heart event is detected (step 1802). The heart event may be bigeminy, trigeminy, bradycardias (slow heart rates), tachycardias (fast heart rates), premature ventricular contractions (PVC), multiple PVCs, any kind of arrhythmia or other heartbeat abnormality. The heart event may be detected in step 1802 by monitor logic. For example, the monitor logic may compare the patient's normal heartbeat morphology (wave shape) that has been previously recorded and stored, in either analog or digital format, with the current heartbeat to determine if there is an irregularity. If a heart event is not detected, the monitor continues to repeat step 1802 until a heart event occurs.

If a heart event is detected in step 1802, the monitor records and stores the heart event in event data (step 1804). In one embodiment, the monitor is continuously recording waveforms recorded received from the electrode leads. However, once an event is detected in step 1802, a specified time period before, during, and after the heart event may be recorded. For example, the monitor may store the heart event data as well as thirty seconds before and after the event. The pre-event time frame and post event time frame may be set by default or may be programmed based on the needs and condition of the patient. The sample or recorded data may be stored in analog or digital form. For example, the monitor may use analog to digital converters to convert the representative heartbeats or waveforms into digital data.

Next, the monitor compares the heart event with a database (step 1806). The database may be a program or memory that stores a library of heart events for comparison. The database may be a portion of the memory that specifies the signature, characteristics or parameter of each possible type of heart event. In one embodiment, if the patient has already experienced a confirmed heart event the current event may be compared with the stored event. The recorded heart event may be recorded in digital or analog form based on accuracy of comparison. The database may include a library of heart events that may be compared against the heart event detected in step 1802. In one embodiment, the monitor logic may specify the severity of the event, if known, for reference by a doctor.

The monitor determines whether the heart event is known (step 1808). If the heart event is known, the monitor inserts a heart event categorization in the event data (step 1810). For example, the monitor may insert a header or label that specifies that the recorded heart event is a tachycardia PVC. The data inserted in step 1810, may be useful to a doctor or other medical specialist that may respond to the patient's heart event.

After step 1808 or 1810, the monitor determines whether transmission is possible (step 1812). The monitor may include transmission logic for specifying when and how data is sent from the monitor. In one embodiment, a detected heart event is to be sent immediately once received. As a result, the monitor may need to determine in step 1812, whether a mobile receiver or other transceiver is available. For example, the monitor may detect a status or availability signal when in proximity to a receiving device that indicates that the monitor may transmit the event data. In another embodiment, the transmission logic may specify that heart events are only to be sent at a specified time period. Alternatively, the patient may wear a portable receiver that is used to send the event data using GPRS as soon as received.

If the monitor determines transmission is possible, the monitor transmits the event data to a receiver (step 1814) with the process terminating thereafter. As previously discussed, the event data may be sent to a receiver that retransmits the event data to the doctor. The event data may also be sent directly to the doctor, to a web interface, a server, or other receiving device. As part of step 1814, the monitor may require that a handshake or data receipt confirmation is received. For example, as part of step 1814 once a receipt handshake has been received from the receiver or transceiver, the monitor may delete the event data to make space available for other heart events and other recorded data.

If the monitor determines transmission is not possible in step 1812, the monitor waits for a time period (step 1816) and then again determines whether transmission is possible (step 1812). The event data is maintained until it may be transmitted to a receiver in step 1814. In some cases, the monitor may record multiple heart events before the data may be transmitted because transmission is not possible.

FIGS. 19-23 illustrate examples of pages that may be displayed in a graphical user interface accessible by the patient, doctor or other authorized individual. The graphical user interface may be displayed to the user through the Internet using a web browser, program application, or database executed one more computing devices, such as a personal computer or PDA. The examples shown include pages and fields for doctor's demographics, patient listing, new patient enrollment, set parameters, billing, heart data, activity and event data, and samples of recorded events.

Figure 19:
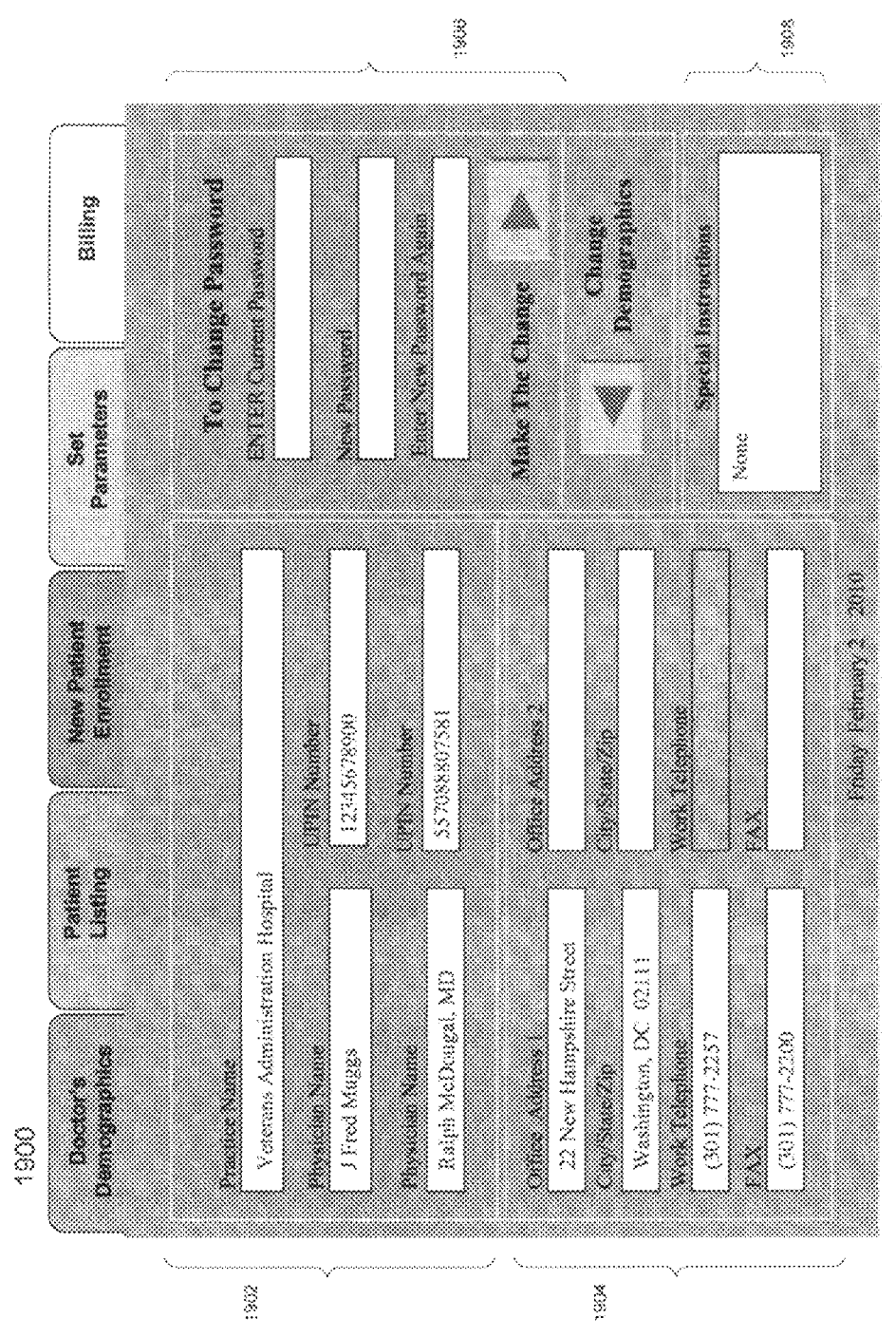

FIG. 19 is an example page for demographics in a graphical user interface in accordance with the illustrative embodiments of the present invention. Page 1900 includes various information, sections, or details that may be used to identify the doctor or other user accessing the page 1900 of the graphical user interface. The page 1900 may include section 1902, section 1904, section 1906, and section 1908.

Section 1902 may include data for identifying the physician which may include a practice name, one or more physician names, and a Unique Physician Identification Number (UPIN) number of each physician.

Section 1904 may specify the address of each doctor including address, telephone number, and other contact information. This may allow the doctor to be contacted in the event a heart event is detected or one physician needs to contact another. Section 1906 may include authorization information for accessing the graphical user interface, page 1900, and other patient information. Section 1908 may include special instructions regarding the doctor or other notices that may be helpful.

Figure 20:
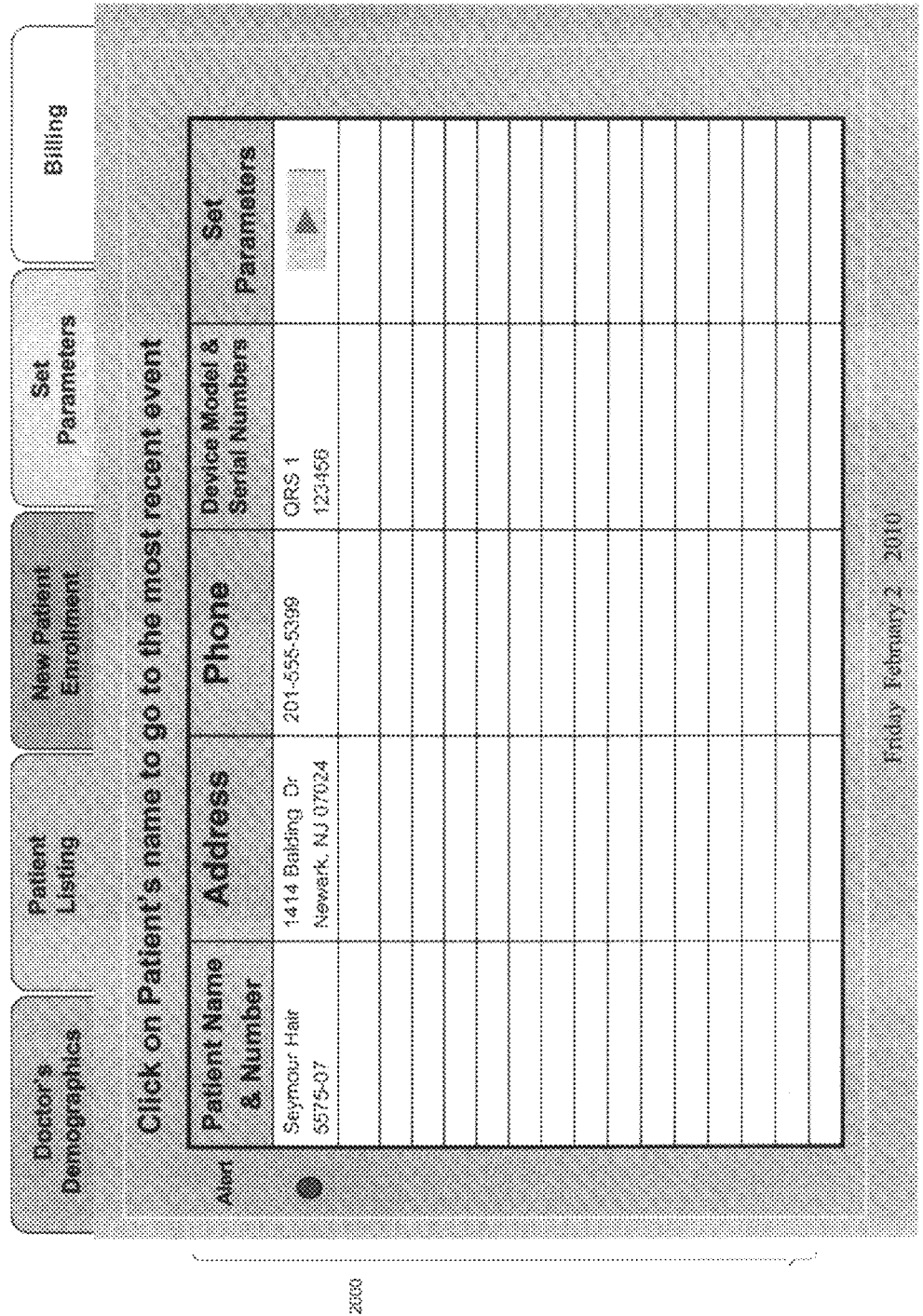
FIG. 20 is an example page for patient listing in a graphical user interface in accordance with the illustrative embodiments of the present invention.

FIG. 20 is an example page for patient listing in a graphical user interface in accordance with the illustrative embodiments of the present invention. Page 2000 may include data for any number of patients. Page 2000 may be particularly useful for tracking numerous patients that are using a monitor. Section 2000 may include various information regarding patients which may include a patient name and number assignment, address, phone, device model and serial number for the monitor, and information for setting parameters. The patient number and device model and serial number may be part of the data that is sent and received from the monitor in order to ensure that the recorded data is properly routed to individuals authorized to see the patient's data.

Figure 21:
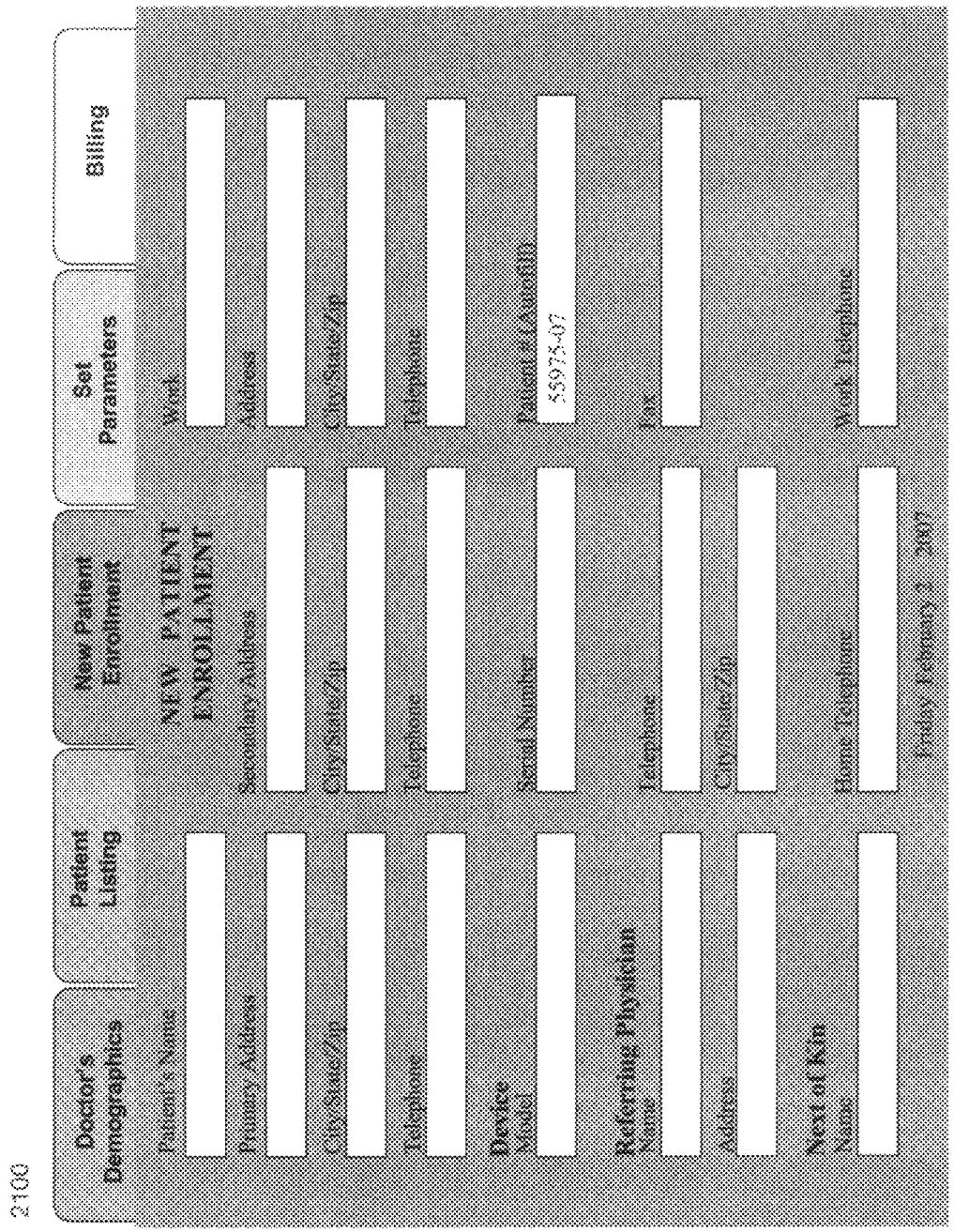
FIG. 21 is an example page for a new patient enrollment in a graphical user interface in accordance with the illustrative embodiments of the present invention.

FIG. 21 is an example page for a new patient enrollment in a graphical user interface in accordance with the illustrative embodiments of the present invention. Page 2100 may be used to enroll a new patient. For example, a patient that has recently had a heart monitor surgically implanted may have his/her patient information entered into page 2100. The information may specify the patient's name, address, contact information, device model, serial number, and patient number, a referring physician, and next of kin. All or a portion of this information may be stored in the memory or storage of the device for transmission from the monitor or receiver. Alternatively, a serial number embedded in the data sent from the monitor may be used to link the data with the patient.

FIG. 22 is an example page for setting parameters in a graphical user interface in accordance with the illustrative embodiments of the present invention. Page 2200 may allow a user to set parameters for the monitoring device or for reviewing the data received. The page 2200 may include the patient information which may specify name, address, contact information, physician, and device information. Page 2200 may also specify monitoring criteria for the monitor.

Monitor criteria may specify parameters that are to be monitored by the heart and important thresholds that may be significant. Monitor criteria may also specify the monitoring of certain heart events, heart rate, and wave form details. In one example, the monitor may monitor the time intervals, slope, amplitude, and rise time between the PR, QRS, QT, and QS points of the heartbeat waveform. The monitoring criteria may further specify what events are important and what conditions may be ignored.

FIG. 23 is an example page for a recorded event in a graphical user interface in accordance with illustrative embodiments of the present invention. Page 2300 may be displayed to a user when a heart event or other data has been received. Page 2300 may include a sample, portion or the entire event as recorded by the heart monitor. Page 2300 may specify patient information, the event date, and the type of monitor. The page 2300 may specify the symptoms, measurements, and other findings. For example, the patient may be experiencing an irregular heartbeat. The monitor detects that the patient's heartbeat is irregular and records the data for immediate or subsequent transmission to the receiver. The receiver may transmit the data to a server or directly to the doctor for review. The doctor may use the data to immediately ascertain the seriousness of the situation in order to provide the patient advice or implement additional medical procedures and medication for the good of the patient.

The previous detailed description is of a small number of embodiments for implementing the invention and is not intended to be limiting in scope. The following claims set forth a number of the embodiments of the invention disclosed with greater particularity.

What is claimed is:

1. A method for determining physiological status of a patient, said method comprising:
   attaching leads to a heart of the patient, wherein one of the leads contacts a right ventricular septum of the heart of the patient;
   detecting the activity level of the patient using one or more piezoelectric accelerometers to determine whether the patient is asleep;
   recording a separate intramyocardial electrogram for each of a right ventricle and a left ventricle of the heart of the patient using the leads in response to signals from the one or more piezoelectric accelerometers when the patient is asleep;
   measuring the amplitude and change in voltage over time of the intramyocardial electrograms;
   stopping the measuring when the patient is not in alpha sleep;
   averaging the amplitude and change in voltage over time measurements for the right ventricle and left ventricle; and
   transmitting the averaged measurements to a receiver for communication to an intended recipient.

2. The method according to claim 1, further comprising:
   attaching the leads to a monitor; and
   implanting the monitor in the patient;
   wherein the amplitude and change in voltage over time of the intramyocardial electrograms for the right ventricle and the left ventricle are measured by the monitor.

3. The method according to claim 2, wherein the monitor includes the one or more piezoelectric accelerometers.

4. The method according to claim 1, wherein the leads include one or more additional piezoelectric accelerometers configured to electromechanically detect heart movement.

5. The method according to claim 1, wherein the measuring step is performed any of simultaneously for the left ventricle and right ventricle and individually for the left ventricle and right ventricle.

6. The method according to claim 1, wherein the transmitting further comprises:
   transmitting a representative sample rhythm to the receiver.

7. The method according to claim 1, wherein the averaging further comprises:
   averaging the measurements for the amplitude and change in voltage over time for the right ventricle and left ventricle after a predefined number of heartbeats.

8. The method according to claim 7, wherein the averaging step further comprises:
   calculating an overall average for both ventricles based on the measured averages.

9. The method according to claim 8, further comprising:
   performing the calculating in response to meeting a measurement threshold.

10. The method according to claim 1, wherein the change in voltage over time includes the slope and rise time.

11. The method according to claim 1, further comprising:
    detecting a heart event; and
    recording the heart event for subsequent transmission in response to detecting the heart event.

12. The method according to claim 11, wherein detecting the heart event comprises:
    measuring the performance of the heart;
    comparing the measurements of the performance of the heart against a library of heart events to determine whether the heart event is occurring.

13. The method according to claim 11, further comprising:
    transmitting the recording of the heart event to the receiver for notifying an individual the heart event has occurred in response to determining transmission is possible;
    displaying the heart event and patient information to the individual using a graphical user interface.

14. The method according to claim 1, further comprising:
    monitoring lung sounds acoustically using the piezoelectric accelerometer.

15. The method according to claim 1, wherein the leads comprise screw-in myocardial leads.

16. The method according to claim 2, wherein the monitor has a frequency response of 2-3 Hz at a low end to 250-300 Hz at an upper end.

17. The method according to claim 2, wherein the monitor includes a band pass filter having a center frequency of approximately 200 Hz.

18. The method according to claim 1, wherein detecting the activity level of the patient includes measuring the activity variance (dA/dr) of the patient.

19. The method according to claim 2, wherein the monitor further measures at least one of awake time, activity amplitude, and activity duration of the patient.

20. The method according to claim 1, wherein determining whether the patient is sleeping comprises comparing the detected activity level of the patient with an activity threshold.

21. The method according to claim 20, further comprising adjusting the activity threshold based on activity level of the patient.

22. The method according to claim 1, wherein one of the leads is positioned to detect right ventricular contractions and right ventricular depolarization signals and one of the leads is positioned to detect left ventricular contractions and left ventricular depolarization signals.

23. The method according to claim 2, wherein the monitor includes telemetry circuitry configured to transmit the averaged measurements to the receiver.

24. The method according to claim 1, wherein the amplitude and change in voltage over time of the intramyocardial electrograms are measured for a predefined number of heartbeats at a specified time interval.

25. The method according to claim 1, wherein the amplitude and change in voltage over time of the intramyocardial electrograms are measured when the patient is in alpha sleep.

26. The method according to claim 2, wherein the monitor further measures the temperature of the patient.

27. The method according to claim 1, further comprising transmitting data from the receiver to a network.

28. The method according to claim 27, further comprising communicating data from the network to a computer.

* * * * *